United States Patent
Srinivasan et al.

(10) Patent No.: US 7,365,124 B2
(45) Date of Patent: Apr. 29, 2008

(54) FLAME RETARDANT RESIN BLENDS BASED ON POLYMERS DERIVED FROM 2-HYDROCARBYL-3,3-BIS(4-HYDROXYARYL)PHTHALIMIDINE MONOMERS

(75) Inventors: Veeraraghavan Srinivasan, Bangalore (IN); Chandrashekhar Lingannaiah, Bangalore (IN); Anantharaman Dhanabalan, Bangalore (IN)

(73) Assignee: General Electric Company, Schenectady, NY (US)

(*) Notice: Subject to any disclaimer, the term of this patent is extended or adjusted under 35 U.S.C. 154(b) by 304 days.

(21) Appl. No.: 10/925,041

(22) Filed: Aug. 24, 2004

(65) Prior Publication Data

US 2005/0228137 A1    Oct. 13, 2005

Related U.S. Application Data

(63) Continuation-in-part of application No. 10/815,880, filed on Mar. 31, 2004, now Pat. No. 7,277,230.

(51) Int. Cl.
C08G 64/00 (2006.01)
C08L 69/00 (2006.01)

(52) U.S. Cl. ............... 525/58; 525/60; 525/64; 525/66; 525/67; 525/68; 525/133; 525/433; 525/439; 525/453; 525/461; 525/462; 525/464; 525/465; 525/466; 525/467; 525/469

(58) Field of Classification Search ............... 525/58, 525/60, 64, 66, 67, 68, 133, 433, 439, 453, 525/461, 462, 464, 465, 466, 467, 469
See application file for complete search history.

(56) References Cited

U.S. PATENT DOCUMENTS 3,671,487 A    6/1972 Visvaldis
3,723,373 A    3/1973 Lucas
4,134,936 A    1/1979 Byrne et al.
4,217,438 A    8/1980 Brunelle et al.
4,310,652 A    1/1982 DeBona et al.
5,132,359 A    7/1992 Sasaki et al.
5,344,910 A    9/1994 Sybert
5,387,629 A    2/1995 McGrath et al.
5,455,310 A    10/1995 Hoover et al.
5,804,525 A    9/1998 Boden et al.
7,135,577 B2    11/2006 Rai et al.
2003/0109650 A1    6/2003 Campbell et al.
2005/0222334 A1    10/2005 Srinivasan et al.
2005/0228137 A1    10/2005 Srinivasan et al.

FOREIGN PATENT DOCUMENTS

| EP | 0 025 859 A2 | 8/1980 |
|---|---|---|
| JP | 3-70790 | 3/1991 |
| JP | 2820277 B2 | 3/1991 |
| JP | 06-003838 | 1/1994 |
| JP | 06-082624 | 3/1994 |
| JP | 2005068216 A | 3/2005 |

OTHER PUBLICATIONS

Lin and Pearce, "Polymers with Improved Flammability Characteristics. I. Phenolphthalein-Related Homopolymers" Journal of Polymer Science: Polymer Chemistry Edition, vol. 19, 2659-2670 (1981).

Lin and Pearce, "Thermal Degradation Study of Phenolphthalein Polycarbonate" Journal of Polymer Science: Polymer Chemistry Edition, vol. 19, 2773-2797 (1981).

Korshak, V.V. et al, "Cardo Polymers" Reviews in Macromolecular Chemistry, Marcel Dekker, Inc., New York, vol. C1, No. 1, (1974), pp. 45-142.

R. Albert, "Phenol Phtaleinanilide and Orcin Phtaleinanilide"; Statement from the chemical laboratory of the University of Erlangen, Received Dec. 28, 3 pgs.

*Primary Examiner*—Ana Woodward

(57) ABSTRACT

A polymer blend consisting essentially of at least one thermoplastic polymer, and a polymer comprising structural units derived from a 2-hydrocarbyl-3,3-bis(4-hydroxyaryl) phthalimidine is disclosed.

31 Claims, No Drawings

FLAME RETARDANT RESIN BLENDS BASED ON POLYMERS DERIVED FROM 2-HYDROCARBYL-3,3-BIS(4-HYDROXYARYL)PHTHALIMIDINE MONOMERS

CROSS REFERENCE TO RELATED APPLICATIONS

The present application claims priority to and is a continuation-in-part of U.S. patent application Ser. No. 10/815,880 filed on Mar. 31, 2004 now U.S. Pat. No. 7,277,230, incorporated herein by reference in its entirety.

BACKGROUND

The present disclosure generally relates to resin blends and articles comprising thermoplastic polymers derived from 2-hydrocarbyl-3,3-bis(4-hydroxyaryl)phthalimidine monomers. More particularly, the present disclosure relates to resin blends and articles comprising a polycarbonate comprising structural units derived from phenolphthalein derivatives, such as 2-hydrocarbyl-3,3-bis(4-hydroxyaryl) phthalimidine monomer and an ABS (acrylonitrile-butadiene-styrene) resin. Still more particularly, the present disclosure relates to resin blends and articles comprising a polycarbonate comprising structural units derived from relatively pure 2-hydrocarbyl-3,3-bis(4-hydroxyaryl)phthalimidine.

It is well known that plastic substrates are rendered fire-retardant by the use of fire-retardant additives. Polymer blends comprising an ABS resin, such as for example, a polycarbonate-ABS blend are particularly challenging substrates due to the inherently high flammability of the ABS resin component. Blends of polycarbonates with styrenic polymers, such as the ABS resins mentioned above are typically rendered fire-retardant by the addition of organic phosphorus compounds, such as resorcinol 1,3-diphenylphosphate (abbreviated as "RDP" throughout this disclosure) and bisphenol A bis(diphenyl)phosphate (abbreviated as "BPADP"), which are generally believed to act in a vapor phase by quenching free radicals that can be responsible for the propagation of the fire. It is also known that an effective amount of the organic phosphorus compound necessary for achieving a given degree of fire retardance can be reduced by employing appropriate synergists, such as siloxanes, inorganic fillers, etc.

Further, for resin blends comprising highly flammable polymers, such as the ABS resins, it is necessary to add relatively large amounts, sometimes as high as the amount of the ABS resin present in the resin blend to achieve robust flame performance (such as for example, the Underwriter Laboratories' rating of "V0" as defined in a UL94 standard) for molded parts having relatively thin walls (example, less than or equal to 2 millimeters wall thickness. However, the addition of relatively high amounts of the fire-retardant additives based on organic phosphorus compounds can lead to number of disadvantages in the final blend, such as for example, inferior heat characteristics (heat distortion temperature) due to the plasticizing effect of the organic phosphorus compounds; poor mechanical properties, such as room temperature impact and tensile modulus, among others. Also, these additives are known to bloom to the surface during aging, thereby resulting in poor aesthetics. Further, there are environmental health and safety concerns during operations, such as for example, during processing, incineration, or recycling of plastic materials containing organic phosphorus-based compounds as fire-retardants. These concerns have prompted the industry to seek alternative, "greener", or more environmentally friendly fire-retardants. Due to the wide applications of fire-retardant plastics for modern day living, a safer and more environmentally friendly non-phosphorus fire-retardant additive would be greatly beneficial to the plastics manufacturing and processing industries. In particular, such a fire-retardant additive will be able to enhance the utility (for example, in the consumer products industry) of polymer blends based on ABS resins, such as for example, the polycarbonate-ABS blend.

Therefore, there is a need for fire-retardant polymer blends containing effective fire-retardant additives that not only are phosphorus-free, but also do not affect the desired physical properties of the blends, such as for example, impact, tensile modulus, and the like. Further, there is a need for polymeric fire-retardant additives that can help retain the properties of the polymer blend, as compared to the low molecular weight fire-retardant additives, such as RDP and BPADP, which act as plasticizers, as described previously.

Phenolphthalein has been used as an aromatic dihydroxy compound monomer for preparing polycarbonates, which are generally characterized with excellent ductility and high glass transition temperatures. Certain derivatives of phenolphthalein have also been used as aromatic dihydroxy compound monomers to prepare polycarbonate resins as well as polyarylate resins. For example, polycarbonate homopolymers have been prepared by an interfacial polycondensation method using phosgene and monomers such as 3,3-bis(4-hydroxyphenyl)phthalimidine and 2-phenyl-3,3-bis(4-hydroxyphenyl)phthalimidine (hereinafter sometimes referred to as "para,para-PPPBP").

Lin and Pearce (Journal of Polymer Science: Polymer Chemistry Edition, (1981) Vol. 19, pp. 2659-2670) reported the synthesis of para, para-PPPBP for preparing polycarbonates and other polymers by refluxing phenolphthalein and aniline hydrochloride in aniline for 6 hours, followed by recrystallization from ethanol. During this reaction, side products are created which, if not removed, can result in para, para-PPPBP having an unacceptable purity for use as a monomer or as a comonomer. The undesirable side products or impurities generally include both inorganic and organic species. With regard to the manufacture of polycarbonate, the impurities can hinder polymerization and result in low weight average molecular weight polycarbonates, example, less than about 22,000 Daltons for melt polymerization and less than about 50,000 Daltons for an interfacial polymerization that exhibit undesirable physical properties, such as increased brittleness, that is, poor ductility properties. Furthermore, the impurities in the para, para-PPPBP monomer include, for example, trace (parts per million) levels of phenolphthalein or phenolphthalein residues that can undesirably produce discoloration in the polycarbonates and other polymers derived therefrom, thereby affecting the transparency of the polymer product. Coloration is not desirable for many commercial applications. U.S. Pat. No. 5,344,910 discloses that copolymers of para, para-PPPBP were found to have poor melt stability resulting in foamy polymer melts and moldings, and discoloration of the resin during melt processing.

It would therefore be desirable to develop a process for preparing relatively pure phenolphthalein derivatives such as 2-hydrocarbyl-3,3-bis(4-hydroxyaryl)phthalimidine, which can then be used for producing polycarbonates and other polymers having improved properties, such as lower color, e.g., a low yellowness index (YI) of less than about 10, and higher weight average molecular weight. Further still, there is a need for such resin blends and articles having excellent fire retardance and improved physical properties.

BRIEF SUMMARY

One aspect of the disclosure is a polymer blend consisting essentially of at least one thermoplastic polymer and a polymer comprising structural units derived from a 2-hydrocarbyl-3,3-bis(4-hydroxyaryl)phthalimidine.

A second aspect of the disclosure is a molded article comprising a polymer blend, the polymer blend consisting essentially of at least one thermoplastic polymer in an amount of 5 to 98 weight percent, a rubber-modified graft copolymer in an amount of 75 to 1 weight percent, and a polycarbonate comprising structural units derived from a 2-hydrocarbyl-3,3-bis(4-hydroxyaryl)phthalimidine in an amount of 20 to 1 weight percent, wherein the weight percents are based on the overall weight of the polymer blend. The at least one thermoplastic polymer can be selected from the group consisting of vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, aromatic polyesters, polyestercarbonate, copolymers comprising aromatic ester, estercarbonate, and carbonate repeat units, mixtures; and blends comprising at least one of the foregoing polymers.

A third aspect of the disclosure is a molded article comprising a polymer blend, where the polymer blend consists essentially of: of a bisphenol A polycarbonate in an amount of 5 to 98 weight percent of an acrylonitrile-butadiene-styrene resin in an amount of 75 to 1 weight percent, and a polycarbonate comprising structural units derived from a 2-phenyl-3-{(4-hydroxyphenyl)(2-hydroxyphenyl)}phthalimidine in an amount of 20 to 1 weight percent, wherein the weight percents are based on an overall weight of the polymer blend.

A fourth aspect of the disclosure is a polymer blend comprising at least one thermoplastic polymer, and a 2-phenyl-3,3-bis(4-hydroxyphenyl)phthalimidine/BPA polycarbonate copolymer in an amount greater than 7 weight percent of the total weight of the blend, wherein the polymer blend is free of a fire retardant phosphorous containing compound, and has at least a V-1 fire rating as measured in accordance with Underwriter Laboratories UL-94 Vertical Burn Test procedure dated, Jul. 29, 1997.

A fifth aspect of the disclosure is a polycarbonate-acrylonitrile-butadiene-styrene polymer blend comprising a bisphenol A polycarbonate; an acrylonitrile-butadiene-styrene resin; and a 2-phenyl-3,3-bis(4-hydroxyphenyl)phthalimidine/bisphenol A polycarbonate copolymer in an amount greater than 7 weight percent of the total weight of the polymer blend, wherein the polymer blend is free of a fire retardant phosphorous containing compound and has a V-0 fire rating as measured in accordance with Underwriter Laboratories UL-94 Vertical Burn Test procedure dated Jul. 29, 1997.

A sixth aspect of the disclosure is a polymer blend comprising at least one thermoplastic polymer and a polymer comprising structural units derived from a 2-hydrocarbyl-3,3-bis(4-hydroxyaryl)phthalimidine, where the blend does not comprise a flame retardant.

The above described and other features are exemplified by the following detailed description.

DETAILED DESCRIPTION

For the purposes of this disclosure, the term "hydrocarbyl" is defined herein as a monovalent moiety formed by removing a hydrogen atom from a hydrocarbon. Representative hydrocarbyls are alkyl groups having 1 to 25 carbon atoms, such as methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; aralkyl groups having 7 to 25 carbon atoms, such as ring-substituted and ring-unsubtituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl" as used herein refers to various forms of aryl groups that have been described hereinabove for the "hydrocarbyl" group.

The present disclosure is generally directed to producing and purifying phenophthalein derivatives, which are suitable for use as monomers for preparing polymers. Further, the prepared polymers are used in blends with other thermoplastic polymers, such as an ABS resin, to form molding compositions, which are in turn valuable for producing articles having excellent fire retardance and physical properties.

Exemplary phenophthalein derivatives are 2-hydrocarbyl-3,3-bis(4-hydroxyaryl)phthalimidines of formula (I):

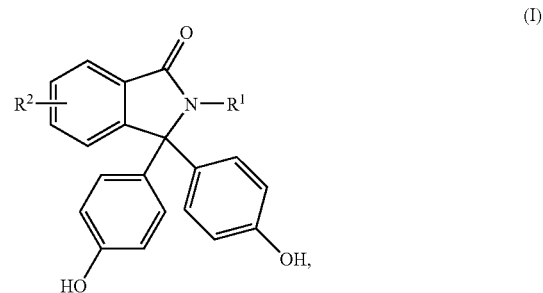

(I)

wherein $R^1$ is selected from a group consisting of a hydrogen and a hydrocarbyl group, and $R^2$ is selected from the group consisting of a hydrogen, a hydrocarbyl group, and a halogen. By way of example, 2-aryl-3,3-bis(4-hydroxyaryl)phthalimidines can generally be prepared by reaction of an aromatic amine (also referred to herein as "aryl amine"), e.g., an aniline, of formula (II):

(II)

wherein $R^1$ is as defined above; with a phenolphthalein of formula (III):

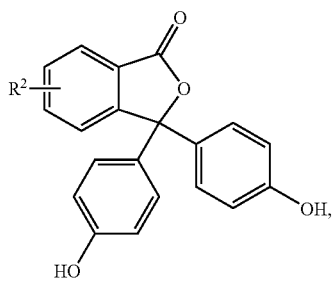

(III)

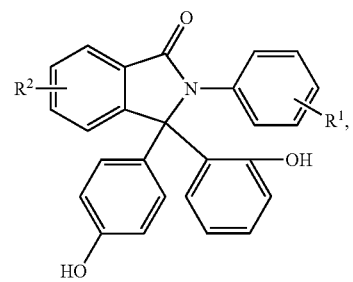

(IV)

wherein R² is as previously defined. An acid catalyst is generally used to facilitate formation of the phthalimidine product. Suitable acid catalysts that can be used include amine salts of mineral acids. Examples of suitable mineral acids include hydrochloric acid, sulfuric acid, and nitric acid. Examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. Hydrochloride salts of the primary aromatic amines of formula (II) are preferred since the amines of formula (II) also serve as the starting material for preparing the phthalimidines of formula (I). In one embodiment, the catalyst is introduced as a pre-formed salt into the reactor. In another embodiment, the catalyst is generated in the reactor by first charging the amine of formula (II) into the reactor, and then adding about ⅓ to about 1 part by weight of an appropriate mineral acid to phenolphthalein. In still another embodiment, about 0.1 parts to about 0.3 parts by weight of hydrogen chloride gas is introduced into a reactor charged with the aryl amine to form an appropriate amount of the aryl amine hydrochloride catalyst. More hydrochloric acid or more hydrogen chloride gas can also used, but is generally not required. A solvent can optionally be employed to form the aryl amine hydrochloride. The solvent can then be removed (if necessary), and the aryl amine of formula (II) can be added, followed by addition of phenolphthalein (III). The reaction of phenolphthalein (III) with the aryl amine (II) proceeds by a condensation reaction to form the desired phthalimidine product (I). An excess of the aryl amine over the phenolphthalein may be used to keep the reaction proceeding in the forward direction. Likewise, a higher reaction temperature with or without removal of water by-product also facilitates product formation. However, in order to enhance the selectivity of 2-hydrocarbyl-3,3-bis(4-hydroxyaryl)phthalimidine (I), and suppress the formation of undesired (2-hydroxyaryl) (4-hydroxyaryl)phthalimidine by-products, for example, it is preferred to control the temperature of the reaction mixture, and the rate of removal of water as well. The temperature of the reaction mixture and rate of water removal is controlled such that the crude 2-hydrocarbyl-3,3-bis(4-hydroxyaryl) phthalimidine product is at least 97.5 area percent pure 2-hydrocarbyl-3,3-bis(4-hydroxyaryl)phthalimidine in one embodiment, and at least 98 area percent pure in another embodiment. The chemical structure of (2-hydroxyaryl) (4-hydroxyaryl)phthalimidine by-product is shown in formula (IV) below.

wherein R¹ and R² are as previously described.

In one embodiment, the reaction temperature is controlled such that the water by-product (calculated based on the moles of the phenolphthalein (III) which is preferably the limiting reagent) distills over a period of about 12 hours to about 20 hours. If the reaction mixture is heated such that the amount of water by-product distills within about 6 hours, the phthalimidine product of formula (I) has a relatively greater amount of the (2-hydroxyaryl) (4-hydroxyaryl)phthalimidine impurity shown in formula (IV). Therefore, although a higher reaction temperature ensures a quicker consumption of the phenolphthalein (El), it also leads to formation of a higher amount of the impurity of formula (IV). If the reaction temperature is not sufficiently high, and water by-product is not removed, a relatively large amount of the phenolphthalein remains unreacted, thereby leading to an inferior product, e.g., forms colored byproducts during melt mixing, forms low molecular weight polymers, and the like. Thus, in one embodiment, the reaction mixture is heated to a temperature of about 150° C. to about 175° C. to remove water by-product and form the 2-hydrocarbyl-3,3-bis(4-hydroxyaryl)phthalimidine product. In another embodiment, the reaction mixture is heated to a temperature of about 150° C. to about 170° C.

By way of example, phenolphthalein (R² is H, R³ is phenyl in formula (III)) was reacted with aniline (R³ is H in formula (II)) in the presence of aniline hydrochloride as the catalyst to form 2-phenyl-3,3-bis(4-hydroxyphenyl)phthalimidine (i.e., para,para-PPPBP), as shown in formula (V).

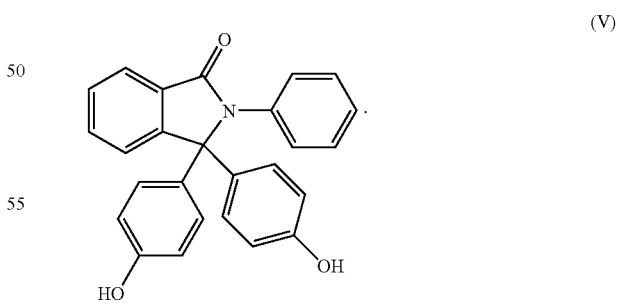

(V)

As will be discussed in the Example Section, the so-formed para, para-PPPBP was produced at high yields and was used to produce polycarbonates with a YI of less than about 10 and high weight average molecular weights. Moreover, the reaction did not produce any detectable (and undesirable) isomers of para, para-PPPBP such as the ortho, para-PPPBP isomer shown in Formula (VI) below.

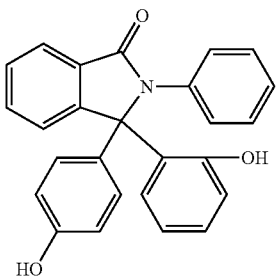

(VI)

Isolation of the desired phenolphthalein derivative from the reaction mixture includes quenching the mixture with an aqueous mineral acid, such as aqueous hydrochloric acid, and precipitating the crude 2-hydrocarbyl-3,3-bis(4-hydroxyaryl)phthalimidine. The crude product is then dissolved in an aqueous inorganic base comprising an alkali metal or alkaline earth metal hydroxide, carbonate, or bicarbonate to provide a first solution. Aqueous sodium hydroxide can be used. Next, the first solution of the crude product is treated with a suitable solid adsorbent that can remove color-forming species present in the solution. In one embodiment, commercially available activated carbon can be used. Treatment with the activated carbon removes color-forming species present in the solution. Suitable activated carbon include, but are not intended to be limited to, the NORIT series of activated carbon available from Norit Corporation, and those activated carbons commercially available from E. Merck Company. The decolorizing efficiency of the activated carbon is indicated by its methylene blue number. Generally, an activated carbon with a relatively higher methylene blue number is less expensive than an activated carbon having a relatively lower methylene blue number. Applicants find that even activated carbons having relatively higher methylene blue numbers are effective decolorizing agents. After treatment with the activated carbon, the resulting mixture is filtered to provide a second solution.

In addition to functioning as a decolorizing agent, the activated carbon treatment also aids in selectively adsorbing the 2-hydrocarbyl-3-{(4-hydroxyaryl) (2-hydroxyaryl)}phthalimidine isomeric impurity. Thus, one method for purifying a crude 2-hydrocarbyl-3,3-bis(4-hydroxyaryl)phthalimidine product comprises contacting an aqueous base solution of the crude product with the activated carbon and filtering off the carbon to provide a second solution. The second solution may again be treated in the same manner, if desired, to provide further reductions in the levels of the 2-hydrocarbyl-3-{(4-hydroxyaryl) (2-hydroxyaryl)}phthalimidine impurity. In an embodiment, the step of treating and filtering the first solution is done such that it is effective to reduce an amount of 2-hydrocarbyl-3-{(4-hydroxyaryl) (2-hydroxyaryl)}phthalimidine to less than or equal to 1,000 parts per million relative to an overall weight of the 2-hydrocarbyl-3,3-bis(4-hydroxyaryl)phthalimidine.

The decolorized and purified solution is next treated with an aqueous mineral acid, such as aqueous hydrochloric acid to precipitate 2-hydrocarbyl-3,3-bis(4-hydroxyaryl)phthalimidine. The precipitate is then finally stirred with an aliphatic alcohol to remove any trace of the phenolphthalein that may still be present and subsequently filtered to furnish purified 2-hydrocarbyl-3,3-bis(4-hydroxyaryl)phthalimidine. Suitable aliphatic alcohols include any aliphatic monohydric or dihydric alcohol. Non-limiting examples of suitable aliphatic alcohols include methanol, ethanol, isopropanol, iso-butanol, n-butanol, tertiary butanol, n-pentanol, iso-pentanol, cyclohexanol, ethylene glycol, propylene glycol, neopentyl glycol and the like. In a particular embodiment, aliphatic monohydric alcohols that are miscible with water, such as methanol, ethanol, and isopropanol are used. Methanol is the preferred aliphatic alcohol for removing phenolphthalein. The so-produced and purified 2-hydrocarbyl-3,3-bis(4-hydroxyaryl)phthalimidine preferably comprises less than or equal to 1,000 parts per million of the 2-hydrocarbyl-3-{(4-hydroxyaryl) (2-hydroxyaryl)}phthalimidine isomeric impurity. Further, the purified 2-hydrocarbyl-3,3-bis(4-hydroxyaryl)phthalimidine preferably comprises less than or equal to 1,000 parts per million of the phenolphthalein starting material.

In another embodiment, a method for purifying crude 2-hydrocarbyl-3,3-bis(4-hydroxyaryl)phthalimidine product comprises dissolving the crude product in an aqueous base solution, treating the aqueous base solution of the crude product with the activated carbon, filtering off the carbon to provide a second solution, and acidifying the second solution with an aqueous acid to precipitate the 2-hydrocarbyl-3,3-bis(4-hydroxyaryl)phthalimidine, which has a relatively low level of the 2-hydrocarbyl-3-{(4-hydroxyaryl) (2-hydroxyaryl)}phthalimidine impurity, e.g., less than 1,000 parts per million. The resulting product can then be contacted with an aliphatic alcohol in the manner previously described.

The general methods described hereinabove can advantageously be applied for preparing para, para-PPPBP having an undetectable level of ortho, para-PPPBP (as measured by HPLC technique). In one embodiment, the purified para, para-PPPBP may also comprise up to 1,000 parts per million of phenolphthalein.

The 2-hydrocarbyl-3,3-bis(4-hydroxyaryl) phthalimidines, including the exemplary 2-phenyl-3,3-bis(4-hydroxyphenyl)phthalimidine, are commercially valuable monomers or comonomers for producing a variety of polymers and polymer compositions formed by reactions of the phenolic OH groups of the 2-hydrocarbyl-3,3-bis(4-hydroxyaryl)phthalimidines. Suitable polymers that can be produced are polymers selected from the group consisting of homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, estercarbonate, and carbonate repeat units; and a polyetherketone. A suitable example of a copolymer comprising aromatic ester, estercarbonate, and carbonate repeat units is the copolymer produced by the reaction of a hydroxy-terminated polyester, such as the product of reaction of isophthaloyl chloride, and terephthaloyl chloride with resorcinol, with phosgene and an aromatic dihydroxy compound, such as bisphenol A.

In one embodiment, polycarbonates having desirable properties are synthesized, wherein the polycarbonates include structural units of formula (VII):

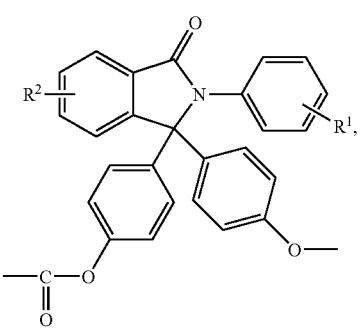

(VII)

which are derived from 2-hydrocarbyl-3,3-bis(4-hydroxyaryl)phthalimidine; wherein $R^1$ and $R^2$ are as described previously; and the C=O structural units are derived from a C=O donor such as phosgene or a carbonic acid diester; where the 2-hydrocarbyl-3,3-bis(4-hydroxyaryl)phthalimidine comprises less than or equal to 1,000 parts per million of a 2-hydrocarbyl-3-{(4-hydroxyaryl) (2-hydroxyaryl)}phthalimidine relative to an overall weight of said 2-hydrocarbyl-3,3-bis(4-hydroxyaryl) phthalimidine.

The polycarbonate composition may further comprise structural units derived from at least one other aromatic dihydroxy compound such as is represented by the general formula (VIII):

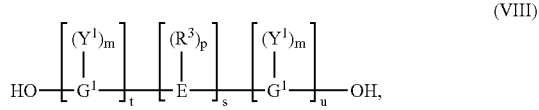

wherein each $G^1$ is an independently aromatic group; E is selected from the group consisting of an alkylene group, an alkylidene group, a cycloaliphatic group, a sulfur-containing linkage group, a phosphorus-containing linkage group, an ether linkage group, a carbonyl group, a tertiary nitrogen group, and a silicon-containing linkage group; $R^3$ is a hydrogen or a monovalent hydrocarbon group each; $Y^1$ is independently selected from the groups consisting of a monovalent hydrocarbyl group, an alkenyl group, an allyl group, a halogen, an oxy group and a nitro group; each m is independently a whole number from zero through the number of positions on each respective $G^1$ available for substitution; p is a whole number from zero through the number of positions on E available for substitution; t is a natural number greater than or equal to one; s is either zero or one; and u is a whole number.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, and adamantylidene; a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy comonomer compound shown in Formula (VIII), when more than one $Y^1$ substituent is present, they may be the same or different. The same holds true for the $R^3$ substituent. Where "s" is zero in formula (VIII) and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ radicals are unsubstituted phenylene radicals; and E is an alkylidene group such as isopropylidene. In particular embodiments, both $G^1$ radicals are p-phenylene, although both may be ortho- or meta-phenylene or one ortho- or meta-phenylene and the other para-phenylene.

Some illustrative, non-limiting examples of aromatic dihydroxy compounds of formula (VIII) include the dihydroxy-substituted aromatic hydrocarbons disclosed by name or formula (generic or specific) in U.S. Pat. No. 4,217,438. Some particular examples of aromatic dihydroxy compound comonomers include, but are not intended to be limited to, 2,4'-dihydroxydiphenylmethane, bis(2-hydroxyphenyl) methane, bis(4-hydroxyphenyl)methane, bis(4-hydroxy-5-nitrophenyl)methane, bis(4-hydroxy-2,6-dimethyl-3-methoxyphenyl)methane, 1,1-bis(4-hydroxyphenyl)ethane, 1,1-bis(4-hydroxy-2-chlorophenyl)ethane, 2,2-bis(4-hydroxyphenyl)propane (bisphenol A); 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 2,2-bis(4-hydroxy-3-ethylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl) cyclohexylmethane, 2,2-bis(4-hydroxyphenyl)-1-phenylpropane, 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(4'-hydroxy-3'methylphenyl) cyclohexane (DMBPC), 1,1-bis(3,5-dimethyl-4-hydroxyphenyl)cyclohexane; 4,4'-[1-methyl-4-(1-methyl-ethyl)-1,3-cyclohexandiyl]bisphenol (1,3 BHPM), 4-[1-[3-(4-hydroxyphenyl)-4-methylcyclohexyl]-1-methyl-ethyl]-phenol (2,8 BHPM), 3,8-dihydroxy-5a,10b-diphenylcoumarano-2',3',2,3-coumarane (DCBP), 2-phenyl-3,3-bis(4-hydroxyphenyl)phthalimidine, 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4- hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-bis(4-hydroxyphenyl)heptane, 4,4'dihydroxy-1,1-biphenyl;4,4'-dihydroxy-3,3'-dimethyl-1,1-biphenyl; 4,4'-dihydroxy-3,3'-dioctyl-1,1-biphenyl; 4,4'-(3,3,5-trimethylcyclohexylidene)diphenol, 4,4'-bis(3,5-dimethyl)diphenol, 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl)benzene, 1,4-bis(2-(4-hydroxy-3-methylphenyl)-2-propyl)benzene 2,4'-dihydroxyphenyl sulfone, 4,4'-dihydroxydiphenylsulfone (BPS), bis(4-hydroxyphenyl)methane, 2,6-dihydroxy naphthalene; hydroquinone; resorcinol, C1-3 alkyl-substituted resorcinols, 3-(4-hydroxyphenyl)-1,1,3-trimethylindan-5-ol, 1-(4-hydroxyphenyl)-1,3,3-trimethylindan-5-ol, and 2,2,2',2'-tetrahydro-3,3,3',3'-tetramethyl-1,1'-spirobi[1H-indene]-6,6'-diol. The most typical aromatic dihydroxy compound is Bisphenol A (BPA).

In some embodiments, an isosorbide comonomer can be used with the 2-hydrocarbyl-3,3-bis(4-hydroxyaryl)phthalimidine monomer to produce polycarbonate copolymers. Isosorbide, sometimes also called 1,4:3,6-dianhydo-D-glucitol, is a rigid, chemically, and thermally stable aliphatic diol that tends to produce copolymers having higher glass transition temperatures, as compared to comonomer compositions which do not include isosorbide.

The carbonic acid diester described above has the general formula (IX):

$$(ZO)_2C=O \qquad (IX),$$

wherein each Z is independently an unsubstituted or substituted alkyl radical, or an unsubstituted or substituted aryl radical. Suitable examples of carbonic acid diesters include, but are not intended to be limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations of two or more carbonic acid diesters thereof. Diphenyl carbonate is widely used as a carbonic acid diester due to its low cost and ready availability on a commercial scale. If two or more of the carbonic acid diesters listed above are utilized, preferably one of the carbonic acid diesters is diphenyl carbonate.

Suitable carbonic acid diesters include the group of "activated aromatic carbonates". As used herein, the term "activated aromatic carbonate" is defined as a diaryl carbonate that is more reactive than diphenyl carbonate in a transesterification reaction. Such activated aromatic carbonates can also be represented by formula (IX), wherein each Z is an aryl radical having 6 to 30 carbon atoms. More specifically, the activated carbonates have the general formula (X):

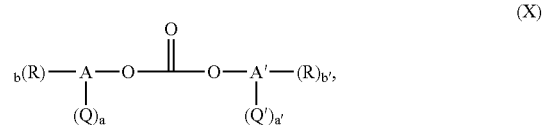

wherein Q and Q' are each independently an ortho-positioned activating group; A and A' are each independently aromatic rings which can be the same or different depending on the number and location of their substituent groups, and a and a' is zero to a whole number up to a maximum equivalent to the number of replaceable hydrogen groups substituted on the aromatic rings A and A' respectively, provided a+a' is greater than or equal to 1. R and R' are each independently substituent groups such as alkyl, substituted alkyl, cycloalkyl, alkoxy, aryl, alkylaryl, cyano, nitro, or halogen. The term b is zero to a whole number up to a maximum equivalent to the number of replaceable hydrogen atoms on the aromatic ring A minus the number a, and the number b' is zero to a whole number up to a maximum equivalent to the number of replaceable hydrogen atoms on the aromatic ring A' minus the number a'. The number, type and location of R or R' on the aromatic ring is not intended to be limited unless they deactivate the carbonate and lead to a carbonate that is less reactive than diphenyl carbonate.

Non-limiting examples of suitable ortho-positioned activating groups Q and Q' include (alkoxycarbonyl)aryl groups, (arylketone)aryl groups, halogens, nitro groups, amide groups, sulfone groups, sulfoxide groups, or imine groups with structures indicated below:

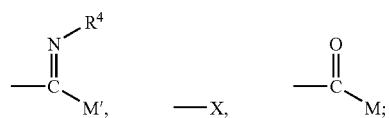

wherein X is halogen or $NO_2$; M and M' independently comprises N-dialkyl, N-alkyl aryl, alkyl, or aryl; and $R^4$ is alkyl or aryl.

Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl) carbonate, bis(o-formylphenyl)carbonate. Unsymmetrical combinations of these structures, wherein the substitution number and type on A and A' are different, are also contemplated. A preferred structure for the activated aromatic carbonate is an ester-substituted diaryl carbonate having the formula (XI):

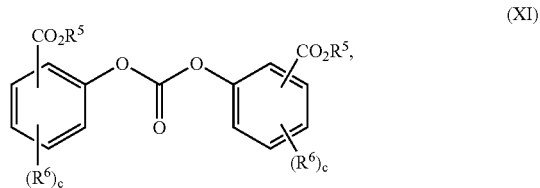

wherein $R^5$ is independently at each occurrence a $C_1$-$C_{20}$ alkyl radical, $C_4$-$C_{20}$ cycloalkyl radical, or $C_4$-$C_{20}$ aromatic radical; $R^6$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and c is independently at each occurrence an integer 0-4. At least one of the substituents $CO_2R^5$ is preferably attached in the ortho position of formula (XI).

Examples of preferred ester-substituted diaryl carbonates include, but are not limited to, bis(methylsalicyl)carbonate (CAS Registry No. 82091-12-1) (also known as BMSC or bis(o-methoxycarbonylphenyl)carbonate), bis(ethyl salicyl) carbonate, bis(propyl salicyl) carbonate, bis(butylsalicyl) carbonate, bis(benzyl salicyl)carbonate, bis(methyl 4-chlorosalicyl)carbonate and the like. Preferably, BSMC is used in melt polycarbonate synthesis due to its lower molecular weight and higher vapor pressure.

Some non-limiting examples of non-activating groups which, when present in an ortho position, would not be expected to result in activated carbonates are alkyl, cycloalkyl or cyano groups. Some specific and non-limiting examples of non-activated carbonates include bis(o-methylphenyl)carbonate, bis(p-cumylphenyl)carbonate, bis(p-(1, 1,3,3-tetramethyl)butylphenyl)carbonate and bis(o-cyanophenyl)carbonate. Unsymmetrical combinations of these structures are also expected to result in non-activated carbonates.

Unsymmetrical diaryl carbonates, wherein one aryl group is activated and one aryl is inactivated, are useful if the activating group renders the diaryl carbonate more reactive than diphenyl carbonate.

One method for determining whether a certain diaryl carbonate is activated or is not activated is to carry out a model melt transesterification reaction between the particular diaryl carbonate and a phenol such as para-(1,1,3,3-tetramethyl)butyl phenol (and comparing the relative reactivity against diphenyl carbonate). This phenol is preferred because it possesses only one reactive site, possesses a low volatility, and possesses a similar reactivity to bisphenol-A. The model melt transesterification reaction is carried out at temperatures above the melting points of the particular diaryl carbonate and phenol in the presence of a transesterification catalyst, which is usually an aqueous solution of sodium hydroxide or sodium phenoxide. Preferred concentrations of the transesterification catalyst are at about 0.001 mole percent based on the number of moles of the phenol or diaryl carbonate. Although a preferred reaction temperature is 200° C., the choice of reaction conditions as well as catalyst concentration can be adjusted depending on the reactivity and melting points of the reactants to provide a convenient reaction rate. The reaction temperature is preferably maintained below the degradation temperature of the reactants. Sealed tubes can be used if the reaction temperatures cause the reactants to volatilize and affect the reactant molar balance. A determination of an equilibrium concentration of the reactants is accomplished through reaction sampling during the course of the reaction with subsequent analysis of the reaction mixture using well-known detection methods such as HPLC (high pressure liquid chromatography). Particular care needs to be taken so that the reaction does not continue after the sample has been removed from the reaction vessel. This is accomplished by cooling down the sample in an ice bath and by employing a reaction quenching acid, such as acetic acid in the water phase of the HPLC solvent system. It may also be desirable to introduce the reaction quenching acid directly into the reaction sample in addition to cooling the reaction mixture. A preferred concentration for the reaction quenching acid, e.g., acetic acid in the water phase of the HPLC solvent system, is about 0.05 mole percent. The equilibrium constant is then determined from the concentration of the reactants and product after equilibrium is reached. Equilibrium is assumed to have been reached when the concentration of components in the reaction mixture reach a point of little or no change on sampling of the reaction mixture. The equilibrium constant can be determined from the concentration of the reactants and products by methods well known to those skilled in the art. A diaryl carbonate which possesses a relative equilibrium constant ($K_{diarylcarbonate}/K_{diphenylcarbonate}$) of greater than 1 is considered to possess a greater reactivity than diphenyl carbonate and is a suitable activated aromatic carbonate for use in the present disclosure, whereas a diaryl carbonate which possesses an equilibrium constant of 1 or less is considered to possess the same or have less reactivity than diphenyl carbonate and is considered not to be activated. It is generally preferred to employ an activated aromatic carbonate with very high reactivity compared to diphenyl carbonate when conducting transesterification reactions. Preferred are activated aromatic carbonates with an equilibrium constant greater than at least 1,000 times that of diphenyl carbonate.

Polycarbonate compositions comprising the structural unit of formula (VII) and carbonate units derived from the activated carbonate preferably comprise at least one end group derived from the activated carbonate. In one embodiment, the end groups which are indicative of the activated aromatic carbonate has a structure of formula (XII):

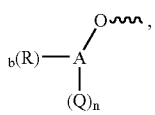
(XII)

wherein Q is an ortho-positioned activating group; A is an aromatic ring, n is a whole number of 1 to the number of replaceable hydrogen groups substituted on the aromatic ring A; R is a substituent group selected from the group consisting of alkyl, cycloalkyl, alkoxy, aryl, cyano, nitro, and halogen; and b is zero to a whole number to the number of replaceable hydrogen groups on the aromatic ring minus n. Q is preferably a radical independently selected from the group consisting of (alkoxycarbonyl)aryl groups, halogens, nitro groups, amide groups, sulfone groups, sulfoxide groups, or imine groups with structures

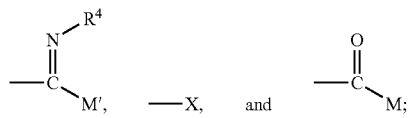

wherein X comprises halogen or $NO_2$, M and M' independently comprises N-alkyl, N-aryl, or N-alkyl aryl; $R^4$ comprises alkyl or aryl when n is 1; and n has a value of 0 or 1.

Polycarbonates prepared using ester-substituted diaryl carbonates, such as for example BMSC, may further comprise very low levels of structural features, which arise from side reactions taking place during the melt polymerization reaction between an ester-substituted diaryl carbonate of structure (XI) and dihydroxy aromatic compounds of structure (VIII). One such structural feature has a structure of formula (XIII):

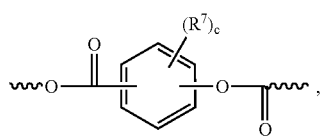
(XIII)

wherein $R^7$ is a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and c is a whole number of 1-4. Typically such kinks are present only to a minor extent (e.g., 0.2 to 1 mole percent).

Structure (XIII) is termed an internal ester-carbonate linkage or kink. Without wishing to be bound by any theory, it is thought that structure (XIII) may arise by reaction of an ester-substituted phenol by-product, for example methyl salicylate, at its ester carbonyl group with a dihydroxy aromatic compound or a hydroxyl group of a growing polymer chain. Further reaction of the ester-substituted phenolic hydroxy group leads to formation of a carbonate linkage. Thus, the ester-substituted phenol by-product of reaction of an ester-substituted diaryl carbonate with a dihydroxy aromatic compound may be incorporated into the main chain of a linear polycarbonate, for example.

Another structural feature present in melt transesterification polymerization reactions between ester-substituted diaryl carbonates and dihydroxy aromatic compounds is the ester-linked terminal end group having a free hydroxyl group and have the structure (XIV):

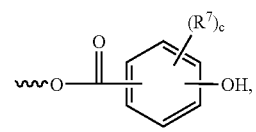
(XIV)

wherein $R^7$ and c are as defined above. Without wishing to be bound by any theory, it is believed that structure (XIV) may arise in the same manner as structure (XIII), but without further reaction of the ester-substituted phenolic hydroxy group. In the structures provided herein, the wavy line represents the polycarbonate polymer chain structure. End capping of the polymer chains made by this method may be only partial. In typical embodiments of polycarbonates prepared by the methods described herein, the free hydroxyl group content is from 7 percent to 50 percent. This number may be varied by changing reaction conditions or by adding additional end-capping agents. In one embodiment, wherein the activated carbonate used is BMSC, there will be an ester linked end group of structure (XV):

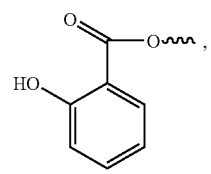
(XV)

which possesses a free hydroxyl group. Thus, for example, if the terminal group of structure (XV) is attached to a para, para-PPPBP unit in the polycarbonate chain then it is designated hereinafter as "p,p-PPPBP-salicyl-OH end", and if the terminal group of structure (XV) is attached to a BPA unit in the polycarbonate chain, it is hereinafter designated as "BPA-salicyl-OH end".

The polycarbonates comprise structural units indicative of the activated carbonate. These structural units may be end groups produced when activated carbonate fragments act as end capping agents or may be kinks introduced into the copolymer by incorporation of activated carbonate fragments.

The polycarbonate made, using the activated aromatic carbonate as described above, may also have end-groups having structure (XVI):

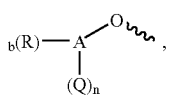

(XVI)

where R, b, A, Q, and n are defined in the preceding sections.

In one embodiment the terminal end group having structure (XVI) is a methyl salicyl group of structure (XVII):

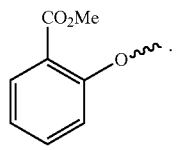

(XVII)

It could also include other salicyl groups such as the ethylsalicyl, isopropylsalicyl, and butylsalicyl groups.

A number of polymerization methods can be used for producing a polymer, such as a homopolycarbonate or a copolycarbonate, comprising structural units derived from a 2-hydrocarbyl-3,3-bis(4-hydroxyaryl)phthalimidine, wherein the 2-hydrocarbyl-3,3-bis(4-hydroxyaryl)phthalimidine comprises less than or equal to about 1,000 parts per million of a 2-hydrocarbyl-3-{(4-hydroxyaryl) (2-hydroxyaryl)}phthalimidine relative to an overall weight of the purified 2-hydrocarbyl-3,3-bis(4-hydroxyaryl)phthalimidine. Suitable methods for fabricating polycarbonates, for example, include a melt transesterification polymerization method, an interfacial polymerization method, and a bis-chloroformate polymerization method.

As used herein, the term "structural units derived from" when used in the context of describing the portions of the copolycarbonates derived from the aliphatic diol and the aromatic dihydroxy compounds refers to the fact that both such monomers lose their respective hydrogen atoms upon incorporation in the polymer.

As used herein the term "activated carbonate" refers to a diaryl carbonate which is typically more reactive (either kinetically or thermodynamically) toward aromatic dihydroxy compounds than diphenyl carbonate under identical conditions. Activated carbonates are typically (but not necessarily) substituted diaryl carbonates.

As used herein the term "structural units indicative of the activated carbonate" means either internal "kinks" in the copolycarbonate or end groups caused by incorporation of a fragment of an activated carbonate such as bismethylsalicyl carbonate (sometimes hereinafter referred to as "BMSC").

The melt transesterification polymerization method is generally carried out by combining a catalyst and a reactant composition to form a reaction mixture; and mixing the reaction mixture under reactive conditions for a time period effective to produce a polycarbonate product, wherein the reactant composition generally comprises a carbonic acid diester of the formula $(ZO)_2C=O$, wherein each Z is independently an unsubstituted or a substituted alkyl radical, or an unsubstituted or a substituted aryl radical and the 2-hydrocarbyl-3,3-bis(4-hydroxyaryl)phthalimidine, wherein the 2-hydrocarbyl-3,3-bis(4-hydroxyaryl)phthalimidine comprises less than or equal to about 1,000 parts per million of a 2-hydrocarbyl-3-{(4-hydroxyaryl) (2-hydroxyaryl)}phthalimidine relative to an overall weight of said 2-hydrocarbyl-3,3-bis(4-hydroxyaryl)phthalimidine.

During the manufacture of the polycarbonates by the melt transesterification method using the activated or unactivated carbonic acid diester, the amount of the carbonic acid diester comprises about 0.8 moles to about 1.30 moles, and more specifically about 0.9 moles to about 1.2 moles, based on one mole of the 2-hydrocarbyl-3,3-bis(4-hydroxyaryl)phthalimidine or any combination of the 2-hydrocarbyl-3,3-bis(4-hydroxyaryl)phthalimidine and at least one aromatic dihydroxy comonomer.

Suitable melt transesterification catalysts include alkali metal compounds, alkaline earth metal compounds, tetraorganoammonium compounds, and tetraorganophosphonium compounds, combinations comprising at least one of the foregoing catalysts.

Specific examples of alkali metal compounds or alkaline earth metal compounds include organic acid salts, inorganic acid salts, oxides, hydroxides, hydrides, and alcoholates of alkali metals and alkaline earth metals. Preferably, the catalyst is an alkali metal compound of the formula $M_1X_1$, wherein $M_1$ is selected from the group consisting of lithium, sodium, and potassium; and $X_1$ is selected from the group consisting of hydroxide and OAr, wherein Ar is a monovalent aromatic radical.

More specifically, examples of suitable alkali metal compounds include, but are not limited to, sodium hydroxide, potassium hydroxide, lithium hydroxide, calcium hydroxide, magnesium hydroxide, sodium bicarbonate, potassium bicarbonate, lithium bicarbonate, sodium carbonate, potassium carbonate, lithium carbonate, sodium acetate, potassium acetate, lithium acetate, lithium stearate, sodium stearate, potassium stearate, lithium hydroxyborate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like.

Specific examples of alkaline earth metal compounds include, but are not limited to, calcium hydroxide, barium hydroxide, magnesium hydroxide, strontium hydroxide, calcium bicarbonate, barium bicarbonate, magnesium bicarbonate, strontium bicarbonate, calcium carbonate, barium carbonate, magnesium carbonate, strontium carbonate, calcium acetate, barium acetate, magnesium acetate, strontium acetate, strontium stearate, and the like.

Exemplary tetraorganoammonium compounds include compounds comprising structure (XVIII):

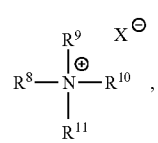

(XVIII)

VI wherein $R^8$-$R^{11}$ are independently a $C_1$-$C_{20}$ alkyl radical, $C_4$-$C_{20}$ cycloalkyl radical or a $C_4$-$C_{20}$ aryl radical and $X^-$ is an organic or inorganic anion. Suitable anions ($X^-$) include hydroxide, halide, carboxylate, sulfonate, sulfate, carbonate and bicarbonate. In one embodiment, the transesterification catalyst comprises tetramethyl ammonium hydroxide.

In still other embodiments, the catalyst is a tetraorganophosphonium compound. Exemplary quaternary phosphonium compounds include compounds comprising structure (XIX):

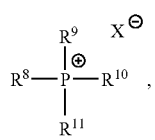

(XIX)

wherein $R^8$-$R^{11}$ and $X^-$ are as previously described. Illustrative anions include hydroxide, halide, carboxylate, sulfonate, sulfate, carbonate, and bicarbonate.

Where $X^-$ is a polyvalent anion such as carbonate or sulfate it is understood that the positive and negative charges in structures (XVIII) and (XIX) are properly balanced. For example, when $R^9$-$R^{12}$ in structure (XVII) are each methyl groups and $X^-$ is carbonate, it is understood that $X^-$ represents $\frac{1}{2}$ ($CO_3^{-2}$) as will be appreciated by those skilled in the art.

Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide, and the like.

In one embodiment, the catalyst comprises tetrabutylphosphonium acetate. In an alternate embodiment, the catalyst comprises a mixture of an alkali metal salt or alkaline earth metal salt with at least one quaternary ammonium compound, at least one quaternary phosphonium compound, or a mixture thereof. For example, the catalyst may be a mixture of sodium hydroxide and tetrabutylphosphonium acetate. In another embodiment, the catalyst is a mixture of sodium hydroxide and tetramethyl ammonium hydroxide.

In another embodiment, the catalyst comprises an alkaline earth metal salt of an organic acid, an alkali metal salt of an organic acid, or a salt of an organic acid comprising both alkaline earth metal ions and alkali metal ions. Alkali metal and alkaline earth metal salts of organic acids, such as for example, formic acid, acetic acid, stearic acid and ethylenediamine tetraacetic acid can also be used. In one embodiment, the catalyst comprises magnesium disodium ethylenediamine tetraacetate (EDTA magnesium disodium salt).

In yet another embodiment, the catalyst comprises the salt of a non-volatile inorganic acid. By "non-volatile" it is meant that the referenced compounds have no appreciable vapor pressure at ambient temperature and pressure. In particular, these compounds are not volatile at temperatures at which melt polymerizations of polycarbonate are typically conducted. The salts of non-volatile acids are alkali metal salts of phosphites; alkaline earth metal salts of phosphites; alkali metal salts of phosphates; and alkaline earth metal salts of phosphates. Suitable salts of non-volatile acids include $NaH_2PO_3$, $NaH_2PO_4$, $Na_2H_2PO_3$, $KH_2PO_4$, $CsH_2PO_4$, $Cs_2H_2PO_4$, or a mixture thereof. In one embodiment, the transesterification catalyst comprises both the salt of a non-volatile acid and a basic co-catalyst such as an alkali metal hydroxide. This concept is exemplified by the use of a combination of $NaH_2PO_4$ and sodium hydroxide as the transesterification catalyst.

Any of the catalysts disclosed above may be used as combinations of two or more substances. The catalyst may be added in a variety of forms. The catalyst may be added as a solid, for example as a powder, or it may be dissolved in a solvent, for example, in water or alcohol. The total catalyst composition is preferably about $1 \times 10^{-7}$ to about $2 \times 10^{-3}$ moles, and with about $1 \times 10^{-6}$ to about $4 \times 10^{-4}$ moles more preferred for each mole of the combination of the purified para, para-PPPBP and the aromatic dihydroxy compound comonomer.

Any of the catalysts described above for use in polycarbonate melt transesterification reactions may be used in reactions involving activated carbonates. It is often advantageous to use a combination of some amount of a salt of an alkaline earth metal and/or an alkali metal (i.e., an "alpha" catalyst) that does not degrade at temperatures used throughout the reaction together with a quaternary ammonium and/or a quaternary phosphonium compound that does degrade at a temperature used in the reaction (i.e., a "beta" catalyst). The total amount of catalyst employed is about $1 \times 10^{-7}$ to about $1 \times 10^{-2}$, and preferably about $1 \times 10^{-7}$ to about $2 \times 10^{-3}$ moles catalyst per total moles of the mixture of para, para-PPPBP and aromatic dihydroxy compound employed.

The reactants for the polymerization reaction using an activated aromatic carbonate can be charged into a reactor either in the solid form or in the molten form. Initial charging of reactants into a reactor and subsequent mixing of these materials under reactive conditions for polymerization may be conducted in an inert gas atmosphere such as a nitrogen atmosphere. The charging of one or more reactant may also be done at a later stage of the polymerization reaction. Mixing of the reaction mixture is accomplished by any methods known in the art, such as by stirring. Reactive conditions include time, temperature, pressure and other factors that affect polymerization of the reactants. Typically, the activated aromatic carbonate is added at a mole ratio of about 0.8 to about 1.3, and more specifically, 0.9 to about 1.2 and all sub-ranges there between, relative to the total moles of aromatic dihydroxy compound and aliphatic diol.

The melt polymerization reaction using the activated aromatic carbonate is conducted by subjecting the above reaction mixture to a series of temperature-pressure-time protocols. In some embodiments, this involves gradually raising the reaction temperature in stages while gradually lowering the pressure in stages. In one embodiment, the pressure is reduced from about atmospheric pressure at the start of the reaction to about 0.01 millibar (1 Pascal) or in another embodiment to 0.05 millibar (5 Pascals) in several steps as the reaction approaches completion. The temperature may be varied in a stepwise fashion beginning at a temperature of about the melting temperature of the reaction mixture and subsequently increased to about 320° C. In one embodiment, the reaction mixture is heated from about ambient (about 21-23° C.) temperature to about 150° C. The polymerization reaction starts at a temperature of about 150° C. to about 220° C., then is increased to about 220° C. to about 250° C. and is then further increased to a temperature of about 250° C. to about 320° C. and all sub-ranges there-between. The total reaction time is about 30 minutes to about 200 minutes and all sub-ranges there between. This procedure will generally ensure that the reactants react to give polycarbonates with the desired molecular weight, glass transition temperature and physical properties. The reaction proceeds to build the polycarbonate chain with production of a by-product such as, for example an ester-substituted alcohol e.g., methyl salicylate. Efficient removal of the by-product may be achieved by different techniques such as reducing the pressure. Generally the pressure starts relatively high in the beginning of the reaction, such as atmospheric pressure in one embodiment, and is lowered progressively throughout the reaction and temperature is raised throughout the reaction. Experimentation is needed to find the most efficient conditions for particular production equipment.

The progress of the reaction may be monitored by measuring the melt viscosity or the weight average molecular weight of the reaction mixture using techniques known in the art such as gel permeation chromatography. These properties may be measured by taking discreet samples or may be measured on-line. After the desired melt viscosity and/or molecular weight is reached, the final polycarbonate product may be isolated from the reactor in a solid or molten form. It will be appreciated by a person skilled in the art, that the method of making polycarbonates as described in the preceding sections may be made in a batch or a continuous process and the process disclosed herein is essentially preferably carried out in a solvent free mode. Reactors chosen should ideally be self-cleaning and should minimize any "hot spots."

In one embodiment, the aliphatic homopolycarbonate and aliphatic-aromatic copolycarbonate may be prepared in an extruder in presence of one or more catalysts, wherein the carbonating agent is an activated aromatic carbonate. The reactants for the polymerization reaction can be fed to the extruder in powder or molten form. In one embodiment, the reactants are dry blended prior to addition to the extruder. The extruder may be equipped with pressure reducing devices (e.g., vents), which serve to remove the activated phenol by-product and thus drive the polymerization reaction toward completion. The molecular weight of the polycarbonate product may be manipulated by controlling, among other factors, the feed rate of the reactants, the type of extruder, the extruder screw design and configuration, the residence time in the extruder, the reaction temperature and the pressure reducing techniques present on the extruder. The molecular weight of the polycarbonate product may also depend upon the structures of the reactants, such as, activated aromatic carbonate, aliphatic diol, dihydroxy aromatic compound, and the catalyst employed. Many different screw designs and extruder configurations are commercially available that use single screws, double screws, vents, back flight and forward flight zones, seals, side-streams and sizes. One skilled in the art may have to experiment to find the best designs using generally known principals of commercial extruder design. Vented extruders similar to those that are commercially available may also be used.

The process disclosed herein can be used to prepare PPPBP homopolycarbonate and copolycarbonates having a weight average molecular weight (Mw) of about 3,000 to about 150,000 and a glass transition temperature (Tg) of about 80° C. to about 300° C. The number average molecular weights (Mn) of the homopolycarbonate and copolycarbonates is from about 1,500 to about 75,000. The transparency of cast films made from the polycarbonate or copolycarbonates prepared in accordance with the present disclosure is greater than about 85 percent, as determined by a Haze Guard Instrument.

In monitoring and evaluating polycarbonate synthesis, it is of particular interest to determine the concentration of Fries product present in the polycarbonate. The generation of significant Fries product can lead to polymer branching, resulting in uncontrollable melt behavior. In the process of preparing polycarbonates described herein, some branching reaction (Fries reaction) takes place (especially at higher temperatures and exacerbated by alpha catalysts) resulting in a Fries product. Fries products are defined as structural units of the product polycarbonate which upon hydrolysis of the product polycarbonate affords a carboxy-substituted dihydroxy aromatic compound bearing a carboxy group adjacent to one or both of the hydroxy groups of the carboxy-substituted dihydroxy aromatic compound. For example, in bisphenol A polycarbonate prepared by a melt polymerization method in which Fries reaction occurs, the Fries product comprises structure (XX) below, which affords 2-carboxy bisphenol A upon complete hydrolysis of the product polycarbonate. As indicated, the Fries product may serve as a site for polymer branching, the wavy lines of structure (XX) indicating a polymer chain structure.

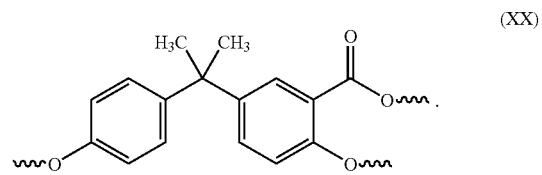

(XX)

The polycarbonates prepared using the activated carbonate by the disclosed method have a concentration of Fries product of less than about 500 parts per million (ppm) as measured by high performance liquid chromatography (HPLC). The Fries concentration is much less than what is obtained in a conventional melt polymerization process that uses diphenyl carbonate as the carbonic acid diester. Fries products are generally undesirable for certain polycarbonates because excessive levels can adversely affect certain physical properties.

In the interfacial polymerization method, 2-hydrocarbyl-3,3-bis(4-hydroxyaryl)phthalimidine, with or without one or more comonomers, and phosgene are reacted in the presence of an acid acceptor and an aqueous base to produce said polycarbonate. Tertiary amines, such as for example, trialkylamines are preferably used as acid acceptors. An exemplary trialkylamine is triethylamine. Suitable aqueous bases include, for example, the alkali metal hydroxides, such as sodium hydroxide. The interfacial method can be used for producing polycarbonates comprising structural units derived from 2-hydrocarbyl-3,3-bis(4-hydroxyaryl)phthalimidine, and preferably having molecular weights greater than about 50,000, relative to polystyrene standard.

The interfacial method described above can be suitably adapted to produce polycarbonates through the intermediate formation of 2-hydrocarbyl-3,3-bis(4-hydroxyaryl)phthalimidine bischloroformate. This method is sometimes called the bischloroformate polymerization method. In one embodiment, the method comprises reacting a 2-hydrocarbyl-3,3-bis(4-hydroxyaryl)phthalimidine with phosgene in an organic solvent, and then reacting the bischloroformate either with a 2-hydrocarbyl-3,3-bis(4-hydroxyaryl)phthalimidine, or an aromatic dihydroxy compound in the presence of an acid acceptor and an aqueous base to form the polycarbonate.

The interfacial polymerization method and the bischloroformate polymerization method can be carried in a batch or a continuous mode using one or more reactor systems. To carry out the process in a continuous mode, one or more continuous reactors, such as for example, a tubular reactor can be used. In one embodiment, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one end-capping agent, optionally one or more solvents, and at least one catalyst. The end-capped polycarbonate thus formed is continuously removed from the tubular reactor system. The process can be used for preparing end-capped polycarbonate oligomers (generally polycarbonates having a weight average molecular weight of less than or equal to 10,000 daltons) or polymers having a weight average molecular weight of greater than 10,000 daltons. The processes outlined hereinabove can also be suitably adapted, for example, to produce end-capped polycarbonates via the intermediate formation of a mixture comprising a bisphenol monochloroformate or a bisphenol bischloroformate.

In another embodiment, polymer blends comprise the polymers described previously and at least one thermoplastic polymer. The at least one thermoplastic polymer is selected from the group consisting of vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, ABS resins, ASA resins, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, tetrafluoroethylene, polycarbonate-polyorganosiloxane block copolymers, copolymers comprising aromatic ester, estercarbonate, and carbonate repeat units; mixtures, and blends comprising at least one of the foregoing polymers.

The polymers and polymer blends described hereinabove are valuable for producing articles. In one embodiment, an article comprises a polymer comprising structural units derived from a 2-hydrocarbyl-3,3-bis(4-hydroxyaryl)phthalimidine, which comprises less than or equal to about 1,000 parts per million of a 2-hydrocarbyl-3-{(4-hydroxyaryl) (2-hydroxyaryl)}phthalimidine, relative to an overall weight of the 2-hydrocarbyl-3,3-bis(4-hydroxyaryl) phthalimidine. In another embodiment, an article comprises a polymer comprising structural units derived from a 2-phenyl-3,3-bis(4-hydroxyphenyl)phthalimidine, which comprises less than or equal to about 1,000 parts per million of 2-phenyl-3-{(4-hydroxyphenyl) (2-hydroxyphenyl)}phthalimidine, relative to an overall weight of said 2-phenyl-3,3-bis(4-hydroxyphenyl)phthalimidine.

Polymers, particularly polycarbonate homopolymers and copolymers comprising structural units derived from the high purity 2-hydrocarbyl-3,3-bis(4-hydroxyaryl)phthalimidine in general, and para,para-PPPBP in particular have a yellowness index (YI) of less than 10 as measured on a 3 millimeter thick plaque in accordance with ASTM D1925 in one embodiment, a YI of less than 5 in another embodiment, and a YI of less than 2 in still another embodiment. Hence, these polycarbonate polymers are useful for producing articles having a number of useful properties, such as a low residual color. The articles also exhibit excellent heat aging. Thus, extruded articles have low color values (as measured by yellowness index, YI) even after heat aging, such as, for example, a YI of less than about 2 after heat aging in air at 155° C.-160° C. for about 500 hours in one embodiment, and a YI of less than about 0.5 after heat aging in air at 120° C. for about 500 hours in another embodiment. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmission, of greater than or equal to about 85 percent. Moreover, the copolycarbonate is especially useful for articles that are preferably made form a polymer having transparency and the other advantageous properties of a BPA homopolycarbonate, but with a significantly higher Tg. Lenses in applications where they are exposed to heat are a good example of such an application.

The polycarbonate compositions disclosed herein are particularly valuable for producing a variety of lenses suitable for diverse applications. In an embodiment, the lens comprises a polycarbonate, which comprises structural units of formula (VII) derived from a 2-hydrocarbyl-3,3-bis(4-hydroxyaryl)phthalimidine comprising less than or equal to about 1,000 parts per million of a 2-hydrocarbyl-3-{(4-hydroxyaryl) (2-hydroxyaryl)}phthalimidine relative to an overall weight of said 2-hydrocarbyl-3,3-bis(4-hydroxyaryl) phthalimidine; and a yellowness index of less than 10 as measured on a 3 millimeter thick plaque in accordance with ASTM D1925 in one embodiment, and less than 2 in another embodiment. Non-limiting examples of suitable articles include an automotive headlamp inner lens, an automotive headlamp outer lens, an automotive fog lamp lens, an automotive bezel, a medical device, a display device, electrical connectors, under the hood automotive parts, and projector lens. Examples of suitable display devices include a laptop computer screen, a liquid crystal display screen, and an organic light-emitting diode display screen.

The polycarbonates disclosed herein may also be combined with effective amounts of one or more of various types of additives used selected from the group consisting of fillers, fire retardants, drip retardants, antistatic agents, UV stabilizers, heat stabilizers, antioxidants, plasticizers, dyes, pigments, colorants, processing aids, and mixtures thereof. These additives are known in the art, as are their effective levels and methods of incorporation. Effective amounts of the additives vary widely, but they are usually present in an amount up to about 50% or more by weight, based on the weight of the entire composition. Especially preferred additives include hindered phenols, thio compounds and amides derived from various fatty acids. The preferred amounts of these additives generally ranges up to about 2% total combined weight based on the total weight of the composition.

In another embodiment, polymer blends consisting essentially of at least one thermoplastic polymer and a polymer comprising structural units derived from a 2-hydrocarbyl-3,3-bis(4-hydroxyaryl)phthalimidine, such as 2-phenyl-3,3-bis(4-hydroxyphenyl)phthalimidine, but which do not contain a fire retardant additive, such as a phosphorus-containing compound (which is traditionally for preparing fire-retardant polymer compositions), surprisingly exhibit excellent fire retardance (a V-0 or V-1 rating in accordance with the standards set forth by Underwriter Laboratories)

without compromising on the other desirable physical properties, such as room temperature impact, tensile modulus, heat distortion temperature or glass transition temperature. Accordingly, one can prepare fire-retardant compositions, molding compositions, and molded articles comprising any polymer that has structural units derived from a 2-hydrocarbyl-3,3-bis(4-hydroxyaryl)phthalimidine. Further, without wishing to be bound by any theory, it is believed that the presence of the impurities in the 2-hydrocarbyl-3,3-bis(4-hydroxyaryl)phthalimidine monomer, such as the 2-hydrocarbyl-3-{(4-hydroxyaryl) (2-hydroxyaryl)}phthalimidine, or the substituted or the unsubstituted phenolphthalein, will not affect the fire-retardance of compositions consisting essentially of flammable thermoplastic polymers and the polymer comprising structural units derived from the 2-hydrocarbyl-3,3-bis(4-hydroxyaryl)phthalimidine. However, depending upon the end-use applications and/or the relative amounts of such a polymer in a final resin blend, the presence of impurities such as the ones described above in the starting monomer may or may not be critical. For other applications, such as for example, molding compositions having a low color, a yellowness index of less than or equal to about 10 (as measured on a 3 millimeter thick plaque in accordance with ASTM D1925) can be obtained without any significant loss in other physical properties by employing a polymer prepared from 2-hydrocarbyl-3,3-bis(4-hydroxyaryl)phthalimidine monomer having less than about 1,000 parts per million of the 2-hydrocarbyl-3-{(4-hydroxyaryl) (2-hydroxyaryl)}phthalimidine, and/or less than or equal to about 1,000 parts per million of the phenolphthalein compound.

Suitable thermoplastic polymers for producing flame retardant compositions include one or more polymers each having structural units derived from one or more monomers selected from the group consisting of vinyl aromatic monomers, monoethylenically unsaturated nitrile monomers, and $C_1$-$C_{12}$ alkyl (meth)acrylate monomers. In an embodiment, rubber-modified graft copolymers and polymers comprising such copolymers are suitable for producing the flame retardant compositions.

Suitable vinyl aromatic monomers include, but are not intended to be limited to, styrene and substituted styrenes having one or more alkyl, alkoxyl, hydroxyl or halo substituent group attached to the aromatic ring, Exemplary vinyl aromatic monomers include, for example, alpha-methyl styrene, p-methyl styrene, vinyl toluene, vinyl xylene, trimethyl styrene, butyl styrene, chlorostyrene, dichlorostyrene, bromostyrene, p-hydroxystyrene, methoxystyrene and vinyl-substituted condensed aromatic ring structures, such as, e.g., vinyl naphthalene, vinyl anthracene, as well as mixtures of vinyl aromatic monomers, among others.

As used in the present context the term "monoethylenically unsaturated nitrile monomer" means an acyclic compound that comprises a single nitrile group and a single site of ethylenic unsaturation per molecule. Suitable monoethylenically unsaturated nitrile monomers include, but are not intended to be limited to, acrylonitrile, methacrylonitrile, and alpha-chloro acrylonitrile.

The terminology "(meth)acrylate monomers" refers collectively to acrylate monomers and methacrylate monomers. Suitable $C_1$-$C_{12}$ alkyl (meth)acrylate monomers include, but are not intended to be limited to, $C_1$-$C_{12}$ alkyl acrylate monomers, e.g., ethyl acrylate, butyl acrylate, iso-pentyl acrylate, n-hexyl acrylate, 2-ethyl hexyl acrylate, and their $C_1$-$C_{12}$ alkyl methacrylate analogs, e.g., methyl methacrylate, ethyl methacrylate, propyl methacrylate, isopropyl methacrylate, butyl methacrylate, hexyl methacrylate, and decyl methacrylate.

In one embodiment, the thermoplastic polymer comprises a vinyl aromatic polymer having structural units derived from one or more vinyl aromatic monomers, for example styrene, and having structural units derived from one or more monoethylenically unsaturated nitrile monomers, for example acrylonitrile. In another embodiment, the thermoplastic polymer comprises from about 55 to about 99 weight percent, and in other embodiments, from about 60 to about 90 weight percent of structural units derived from styrene; and in other embodiments, from about 1 to about 45 weight percent, and in still other embodiments from about 10 to about 40 weight percent of structural units derived from acrylonitrile. In one embodiment, the weight average molecular weight of such types of thermoplastic polymer is from about 50,000 to about 100,000 daltons, relative to polystyrene standards.

The thermoplastic polymer can also comprise at least one rubber modified graft copolymer comprising a discontinuous rubber phase dispersed in a continuous rigid thermoplastic phase, wherein at least a portion of the rigid thermoplastic phase is chemically grafted to the rubber phase. Hereinafter the term "rubber modified graft copolymer" is sometimes referred to as a rubber modified thermoplastic resin. In one embodiment, rubber modified graft copolymers comprise those made by a bulk or, synonymously, a mass polymerization process. In another embodiment, rubber modified graft copolymers comprise those made by emulsion polymerization. Suitable rubbers for use in making the rubber phase comprise those having a glass transition temperature ($T_g$) of less than or equal to 25° C. in one embodiment, less than or equal to 0° C. in another embodiment, and less than or equal to minus 30° C. in yet another embodiment. The rubber comprises a polymer, often a linear polymer, having structural units derived from one or more conjugated diene monomers. Suitable conjugated diene monomers include, but are not intended to be limited to, 1,3-butadiene, isoprene, 1,3-heptadiene, methyl-1,3-pentadiene, 2,3-dimethylbutadiene, 2-ethyl-1,3-pentadiene, 1,3-hexadiene, 2,4-hexadiene, dichlorobutadiene, bromobutadiene, and dibromobutadiene; as well as mixtures of conjugated diene monomers. In other embodiments, the conjugated diene monomer comprises at least one of 1,3-butadiene or isoprene.

In other embodiments, the rubber may optionally include structural units derived from one or more copolymerizable monoethylenically unsaturated monomers selected from $C_2$-$C_8$ olefin monomers, vinyl aromatic monomers, monoethylenically unsaturated nitrile monomers, and $C_1$-$C_{12}$ alkyl (meth)acrylate monomers. As used herein, the term "$C_2$-$C_8$ olefin monomers" means a compound having from 2 to 8 carbon atoms per molecule and having a single site of ethylenic unsaturation per molecule. Suitable $C_2$-$C_8$ olefin monomers comprise, example, ethylene, propene, 1-butene, 1-pentene, and heptene. Suitable vinyl aromatic monomers, monoethylenically unsaturated nitrile monomers, and $C_1$-$C_{12}$ alkyl (meth)acrylate monomers comprise those previously described.

In one embodiment, the rubber is a polybutadiene homopolymer. In another embodiment, the rubber is a copolymer, for example, a block copolymer comprising structural units derived from one or more conjugated diene monomers and up to 50 percent by weight of structural units derived from one or more monomers selected from vinyl aromatic monomers and monoethylenically unsaturated nitrile monomers, such as, for example, a styrene-butadiene copolymer, an acrylonitrile-butadiene copolymer or a styrene-butadiene-acrylonitrile copolymer. More specifically, the rubber can be a styrene-butadiene block copolymer that contains from about 50 to about 95 weight percent of structural units derived from butadiene, and from about 5 to about 50 weight percent of structural units derived from styrene. Suitable rubber polymers may also comprise structural units derived from butyl acrylate. In another embodiment, the rubber is an ethylene-propylene-diene modified rubber.

The elastomeric rubber phase may be made by aqueous emulsion polymerization in the presence of a free radical initiator, a polyacid surfactant, and optionally, a chain transfer agent. The resulting polymer emulsion can be coagulated to form particles of the elastomeric phase material. Suitable free radical include, but are not intended to be limited to, an organic peroxide compound, such as benzoyl peroxide; a persulfate compound, such as potassium persulfate; an azonitrile compound, such as, 2,2'-azobis-2,3,3-trimethylbutyronitrile (sometimes abbreviated in common parlance as "AIBN"); or a redox initiator system, such as a combination of cumene hydroperoxide, ferrous sulfate, tetrasodium pyrophosphate, and a reducing sugar or sodium formaldehyde sulfoxylate. Suitable chain transfer agents include, but are not intended to be limited to, a $C_9$-$C_{13}$ alkyl mercaptan compound, such as nonyl mercaptan, tertiary dodecyl mercaptan, or the like.

The emulsion polymerized particles of the elastomeric rubber phase material can have a weight average particle size in one embodiment of about 50 to about 1,000 nanometers ("nm"), in another embodiment of about 50 to about 800 nm, and in yet another embodiment of from 100 to 500 nm, as measured by light transmission. The size of emulsion polymerized elastomeric particles may optionally be increased by mechanical, colloidal or chemical agglomeration of the emulsion-polymerized particles according to known techniques.

Specific thermoplastic polymers that can be used in a polymer blend with a polymer comprising structural units derived from a 2-hydrocarbyl-3,3-bis(4-hydroxyaryl)phthalimidine can be selected from the group consisting of ABS resins, ASA (acrylate-styrene-acrylonitrile) resins, acrylonitrile-butadiene copolymer, styrene-butadiene copolymers, ethylene-propylene-diene copolymers, and polyacrylates, such as those comprising poly(butyl acrylate) and poly(2-ethylhexyl acrylate).

Examples of suitable bisphenol compounds used for producing the polycarbonate block of formula (XXII) include, but are not intended to be limited to, 4,4'-(3,3,5-trimethylcyclohexylidene)diphenol, 4,4'-bis(3,5-dimethyl)diphenol, 1,1-bis(4-hydroxy-3-methylphenyl)cyclohexane, 4,4-bis(4-hydroxyphenyl)heptane, 2,4'-dihydroxydiphenylmethane, bis(2-hydroxyphenyl)methane, bis(4-hydroxyphenyl)methane, bis(4-hydroxy-5-nitrophenyl)methane, bis(4-hydroxy-2,6-dimethyl-3-methoxyphenyl)methane, 1,1-bis(4-hydroxyphenyl)ethane, 1,1-bis(4-hydroxy-2-chlorophenyl)ethane, 2,2-bis(4-hydroxyphenyl)propane, 2,2-bis(3-phenyl-4-hydroxyphenyl)propane, 2,2-bis(4-hydroxy-3-methylphenyl)propane, 2,2-bis(4-hydroxy-3-ethylphenyl)propane, 2,2-bis(4-hydroxy-3-isopropylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl)cyclohexylmethane, 2,2-bis(4-hydroxyphenyl)-1-phenylpropane, 2,4'-dihydroxyphenyl sulfone, 2,6-dihydroxy naphthalene; hydroquinone; resorcinol, $C_{1-3}$ alkyl-substituted resorcinols, 3-(4-hydroxyphenyl)-1,1,3-trimethylindan-5-ol, 1-(4-hydroxyphenyl)-1,3,3-trimethylindan-5-ol, 2,2,2',2'-tetrahydro-3,3,3',3'-tetramethyl-1,1'-spirobi[1H-indene]-6,6'-diol, 1-methyl-1,3-bis(4-hydroxyphenyl)-3-isopropylcyclohexane, 1-methyl-2-(4-hydroxyphenyl)-3-[1-(4-hydroxyphenyl)isopropyl]cyclohexane, and combinations thereof; and combinations comprising at least one of the foregoing bisphenols.

Non-limiting examples of antioxidants that can be used in molding compositions, for example, include tris(24-di-tert-butylphenyl) phosphite, 3,9-di(2,4-di-tert-butylphenoxy)-2,4,8,10-tetraoxa-3,9-diphosphaspiro[5.5]undecane, 3,9-di(2,4-dicumylphenoxy)-2,4,8,10-tetraoxa-3,9-diphosphaspiro[5.5]undecane, tris(p-nonylphenyl)phosphite, 2,2',2"-nitrilo[triethyl-tris[3,3',5,5'-tetra-tertbutyl-1,1'-biphenyl-2'-diyl]phosphite], 3,9-distearyloxy-2,4,8,10-tetraoxa-3,9-diphosphaspiro[5.5]undecane, dilauryl phosphite, 3,9-di[2,6-di-tert-butyl-4-methyl-phenoxy]-2,4,8,10-tetraoxa-3,9-diphosphaspiro[5.5]undecane and tetrakis(2,4-di-tert-butylphenyl) 4,4'-bis(diphenylene)phosphonite, distearyl pentaerythritol diphosphite, diisodecyl pentaerythritol diphosphite, 2,4,6-tri-tert-butylphenyl-2-butyl-2-ethyl-1,3-propanediol phosphite, tristearyl sorbitol triphosphite, tetrakis(2,4-di-tert-butylphenyl)4,4'-biphenylene diphosphonite, (2,4,6-tri-tert-butylphenyl)-2-butyl-2-ethyl-1,3-propanediolphosphite, tri-isodecylphosphite, and mixtures of phosphites containing at least one of the foregoing. Of these, tris(2,4-di-tert-butylphenyl) phosphite, 2,4,6-tri-tert-butylphenyl-2-butyl-2-ethyl-1,3-propanediol phosphite, bis(2,4-di-tert-butylphenyl)pentaerythritol diphosphite are preferred for some applications, as well as mixtures of phosphites containing at least one of the foregoing phosphites, and the like.

Non-limiting examples of processing aids include Doverlube® FL-599 (available from Dover Chemical Corporation), Polyoxyter® (available from Polychem Alloy Inc.), Glycolube P (available from Lonza Chemical Company), pentaerythritol tetrastearate, Metablen A-3000 (available from Mitsubishi Rayon), neopentyl glycol dibenzoate, and the like.

Non-limiting examples of UV stabilizers include 2-(2'-Hydroxyphenyl)-benzotriazoles, e.g., the 5'-methyl-, 3',5'-di-tert.-butyl-, 5'-tert.-butyl-,5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-alpha-methylbenzyl-5'-methyl, 3'-alpha-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl-, 5-chloro-3',5'-di-tert.-amyl-derivative, and Tinuvin® 234 (available from Ciba Specialty Chemicals); 2,4-bis-(2'-hydroxyphenyl)-6-alkyl-s-triazines, e.g., the 6-ethyl-, 6-heptadecyl- or 6-undecyl-derivative; 2-hydroxybenzophenones e.g., the 4-hydroxy-, 4-methoxy-, 4-octoxy-, 4-decyloxy-, 4-dodecyloxy-, 4-benzyloxy-, 4,2',4'-trihydroxy-, 2,2',4,4'-tetrahydroxy- or 2'-hydroxy-4,4'-dimethoxy-derivative; 1,3-bis-(2'-hydroxybenzoyl)-benzenes, e.g., 1,3-bis-(2'-hydroxy-4'-hexyloxybenzoyl)-benzene, 1,3-bis-(2'-hydroxy-4'-octyloxybenzoyl)-benzene or 1,3-bis-(2'-hydroxy-4'-dodecyloxybenzoyl)-benzene; esters of optionally substituted benzoic acids, e.g., phenylsalicylate octylphenylsalicylate, dibenzoylresorcin, bis-(4-tert.-butylbenzoyl) resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester; acrylates, e.g., alpha-cyano-beta, beta-diphenylacrylic acid-ethyl ester or isooctyl ester, alpha-carbomethoxycinnamic acid methyl ester, alpha-cyano-beta-methyl-p-methoxycinnamic acid methyl ester or -butyl ester or N(beta-carbomethoxyvinyl)-2-methyl-indoline; oxalic acid diamides, e.g., 4,4'-di-octyloxy-oxanilide, 2,2'-di-octyloxy-5,5'-di-tert.-butyl-oxanilide, 2,2'-di-dodecyloxy-5,5-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyloxanilide and the mixture thereof with 2-ethoxy-2'-ethyl-5,4'-di-tert-butyl-oxanilide, or mixtures of ortho- and para-methoxy- as well as of ortho- and para-ethoxy di-substituted oxanilides. In one embodiment, the ultraviolet light absorber can be selected from the group of 2-(2-hydroxy-5-methylphenyl)-2H-benzotriazole; 2-(2-hydroxy-3,5-di-tert-amylphenyl)-2H-benzotriazole; 2-[2-hydroxy-3,5-di-(alpha,alpha-dimethylbenzyl)phenyl]-2H-benzotriazole; 2-(2-hydroxy-5-tert-octylphenyl)-2H-benzotriazole; 2-hydroxy-4-octyloxybenzophenone; nickel bis(O-ethyl 3,5-di-tert-butyl-4-hydroxybenzylphosphonate); 2,4-dihydroxybenzophenone; 2-(2-hydroxy-3-tert-butyl-5-methylphenyl)-2H-benzotriazole;and a nickel butylamine complex with 2,2'-thiobis(4-tert-butylphenol), 2-ethoxy-2'-ethyloxanilide or 2-ethoxy-2'-ethyl-5,5'-ditert-butyloxanilide.

In other embodiments, the fire retardant polymer blends comprise at least one thermoplastic polymer and a 2-phenyl-3,3-bis(4-hydroxyphenyl)phthalimidine/BPA polycarbonate copolymer in an amount greater than 7 weight percent of the total weight of the blend, wherein the polymer blend is free of a fire retardant phosphorous containing compound, and has at least a V-1 fire rating, as measured in accordance with Underwriter Laboratories UL-94 Vertical Bum Test procedure dated Jul. 29, 1997. In other embodiments, depending upon the relative composition of the thermoplastic polymer and the 2-phenyl-3,3-bis(4-hydroxyphenyl)phthalimidine/BPA polycarbonate copolymer, such polymer blends also have a V-1 fire rating, as measured in accordance with Underwriter Laboratories UL-94 Vertical Burn Test procedure dated July 29, 1997. Polymer blends having a V-1 fire rating are also valuable for many commercial applications. An exemplary polymer blend comprises a blend of bisphenol A polycarbonate and an acrylonitrile-butadiene-styrene copolymer as the thermoplastic polymer component. As described in this embodiment, the polymer blend is free of a fire retardant phosphorous containing compound such as, for example, polymeric or non-polymeric organic phosphorus species selected from the group consisting of phosphate esters, thiophosphate esters, phosphonate esters, thiophosphonate esters, phosphinate esters, thiophosphinate esters; phosphines, including triphenylphosphine; phosphine oxides, including triphenylphosphine oxide and tris(2-cyanoethyl)phosphine oxide, thiophosphine oxide; and phosphonium salts. Other organic phosphorus species include, but are not intended to be limited to, non-polymeric phosphate esters including, for example, alkyl phosphate esters, aryl phosphate esters, resorcinol-based phosphate esters, and bisphenol-based phosphate esters. Exemplary organic phosphorus species are aromatic phosphate esters, non-limiting examples of which includes triphenylphosphate, tricresylphosphate, resorcinol bis(diphenylphosphate), bisphenol A bis(diphenylphosphate), tris(nonyl)phenylphosphate, mixtures of the foregoing aromatic phosphate esters, and other aromatic phosphate esters known in the art. In summary, the polymer blend in this embodiment can be free of any phosphorous containing compounds that function as fire retardants. As such, the polymer blend may include phosphorous containing compounds that do not function as fire retardants, e.g., phosphite based additives, and the like.

The fire-retardant compositions may further comprise one or more fluoropolymers in an amount that is effective to provide anti-drip properties to the compositions. Suitable fluoropolymers and methods for making such fluoropolymers are known, such as for example, U.S. Pat. Nos. 3,671,487 and 3,723,373. Suitable fluoropolymers include homopolymers and copolymers that comprise structural units derived from one or more fluorinated alpha-olefin monomers. The term "fluorinated alpha-olefin monomer" means an alpha-olefin monomer that includes at least one fluorine atom substituent. Suitable fluorinated alpha-olefin monomers include, e.g., fluoroethylenes such as, tetrafluoroethylene, trifluoroethylene, 1,1-difluoroethylene, fluoroethylene, 1,1-difluoro-2-chloroethylene, 1,1-difluoro-1,1-dichloroethylene, 1,2-difluoro-1,2-dichloroethylene, 1-fluoro-2,2-dichloroethylene, 1-chloro-1-fluoroethylene, and 1,1,2-trichloro-2-fluoroethylene; and fluoropropylenes, such as e.g., hexafluoropropylene, 1,1,1,3-tetrafluoropropylene, 1,1,1,3,3-pentafluoropropylene, and 1,1,1,2-tetrafluoropropylene. In other embodiments suitable fluorinated alpha-olefin copolymers include copolymers comprising structural units derived from two or more fluorinated alpha-olefin copolymers such as, e.g., poly(tetrafluoroethylene-hexafluoropropylene), and copolymers comprising structural units derived from one or more fluorinated monomers and one or more non-fluorinated monoethylenically unsaturated monomers that are copolymerizable with the fluorinated monomers such as, e.g., poly(tetrafluoroethylene-ethylene-propylene) copolymers. Suitable non-fluorinated monoethylenically unsaturated monomers include e.g., alpha-olefin monomers such as, e.g., ethylene, propylene, butene, acrylate monomers such as e.g., methyl methacrylate, butyl acrylate, vinyl ethers, such as, e.g., cyclohexyl vinyl ether, ethyl vinyl ether, n-butyl vinyl ether, vinyl esters such as, e.g., vinyl acetate, and vinyl versatate. In a particular embodiment the fluoropolymer is a poly(tetrafluoroethylene) homopolymer ("PTFE"). The fluoropolymer can be incorporated in the polymer blends by any of the methods known in the art, such as those disclosed in commonly owned U.S. patent application US 2003/0109650 (published on Jun. 12, 2003).

The flame retardant resinous compositions may optionally comprise at least one impact modifier, which is different from any rubber modified graft copolymer and any rubber in the rubber modified graft copolymer, as described above. In various embodiments, suitable impact modifiers comprise at least one core-shell type impact modifiers comprising a poly(alkyl acrylate) or poly(alkyl methacrylate) shell. In other embodiments, suitable impact modifiers comprise core-shell type impact modifiers comprising a poly(methylmethacrylate) shell. In still other embodiments, suitable impact modifiers comprise those which are core-shell type impact modifiers including a shell comprising poly(methylmethacrylate) and a core comprising a polybutadiene rubber. In still other embodiments, suitable impact modifiers comprise those which are core-shell type impact modifiers including a shell comprising poly(methylmethacrylate) and a core comprising a silicone rubber. Illustrative silicone rubbers may comprise poly(diorganosiloxanes) such as poly(dimethylsiloxane). In other embodiments, suitable impact modifiers comprise those which are core-shell type impact modifiers including a shell comprising poly(methylmethacrylate) and a core comprising a silicone rubber and at least one other polymer with a glass transition temperature higher than that of the silicone rubber. In still other embodiments, suitable impact modifiers comprise those which are core-shell type impact modifiers including a shell comprising poly(methylmethacrylate) and a core comprising a silicone rubber and at least one poly(alkylacrylate) with a glass transition temperature higher than that of the silicone rubber. In a particular embodiment, a suitable impact modifier is a core-shell type impact modifier, such as those which include a shell comprising poly(methylmethacrylate) and a core comprising a silicone rubber and poly(butylacrylate). One type of suitable core-shell impact modifier can be prepared in accordance with the method of Sasaki et al. as taught in U.S. Pat. No. 5,132,359. In some embodiments, suitable impact modifiers include those sold under the trade name METABLEN by Mitsubishi Rayon Co., Ltd.

The fire-retardant compositions described hereinabove are valuable for producing articles. The use of copolymers comprising structural units derived from 2-hydrocarbyl-3,3-bis(4-hydroxyaryl)phthalimidine monomers, such as p,p-PPPBP as a phosphorus-free fire-retardant additive is useful for producing articles, particularly thin-walled fire-retardant articles having a wall thickness of about 1 to about 2 millimeters in one embodiment, and about 2 to about 5 millimeters in another embodiment. Generally, the lower the wall thickness of a molded article, the more difficult it is to achieve effective fire-retardance (e.g., a V-0 UL94 rating), or a desired "flame out time" (abbreviated in this disclosure as "FOT"). An exemplary copolymer, which is very effective as such a polymeric fire-retardant additive is a material comprising structural units derived from a monomer mixture of 75 weight percent of bisphenol A and 25 weight percent of p,p-PPPBP. Such a copolymer can be prepared by any method known in the art for producing polycarbonates (discussed previously).

EXAMPLES

In the following examples, molecular weights were measured by gel permeation chromatography using a polystyrene standard. Glass transition temperatures of the polycarbonates were measured by differential scanning calorimetry by heating the sample at the rate of 10° C. to 20° C. per minute under nitrogen. Yellow index was measured using ASTM D1925 test method on plaques of 3 millimeter thickness and on films of 0.2 millimeter thickness. Films were prepared in a petri dish by casting from a solution of 1.1 grams of a polycarbonate in about 10 milliliters of chloroform.

HPLC analysis was generally carried out by using a solution of about 50 milligrams of the sample dissolved in about 10 milliliters of methanol. The HPLC instrument was equipped with a C18 (reverse phase) column maintained at a temperature of 40° C., and an ultraviolet detector capable of detecting components at a wavelength of 230 nanometers. A solvent mixture of methanol and water of varying relative proportions was used. The flow rate was maintained at 1 milliliter per minute. Area percent assay was computed from the area value for each peak detected in the chromatogram divided by the total area from all peaks detected. To measure weight percent assay, calibration curves for p,p-PPPBP, o,p-PPPBP, and phenolphthalein were first generated. Then, the weight percent of a given component in a sample was calculated using these calibration curves.

All melt transesterification polymerizations were carried out using either diphenyl carbonate or bismethylsalicyl carbonate. The catalyst for all of the polymerization runs was prepared by taking appropriate aliquots of a stock solution of aqueous sodium hydroxide and a 25 weight percent aqueous tetramethylammonium hydroxide. Molded articles were prepared by first preparing pellets of the molding compositions using a 25 millimeter ZSK twin-screw extruder, followed by injection molding using a L&T DEMAG 60 molding machine having a clamping capacity of 60 ton, a screw diameter of 25 millimeters, and shot capacity of 58 grams of polystyrene.

Reference to the polymer blends as shown in Table 4 included one or more of the following materials. Bisphenol A polycarbonate (PC-105), made by an interfacial process and having a weight average molecular weight of 64,000 (polystyrene standard, methylene chloride solvent) was obtained from GE Plastics, Mt. Vernon, Ind. Acrylonitrile-Butadiene-Styrene (ABS) terpolymer resin made by a bulk process was used. The resin has an acrylonitrile content of 21.5-22.5 weight percent, butadiene rubber content of 11-12.5 weight percent, and styrene content of 66-66.5 weight percent. TSAN (Teflon-grafted Styrene-Acrylonitrile copolymer) was used as an anti-drip agent. TSAN was prepared by polymerizing styrene and acrylonitrile in an emulsion of Teflon so as to get partially SAN-encapsulated Teflon particles. The TSAN so prepared typically contains about 50 weight percent of Teflon and about 50 weight percent of styrene and acrylonitrile. Liquid BPADP {(bisphenol A bis(diphenylphosphate)} was purchased from Albermarle Fine and Specialty Chemicals.

In Table 4, "PC-ST" refers to the polyorganosiloxane-polycarbonate block copolymer having a weight average molecular weight of about 57,000 and represented by formula XXI:

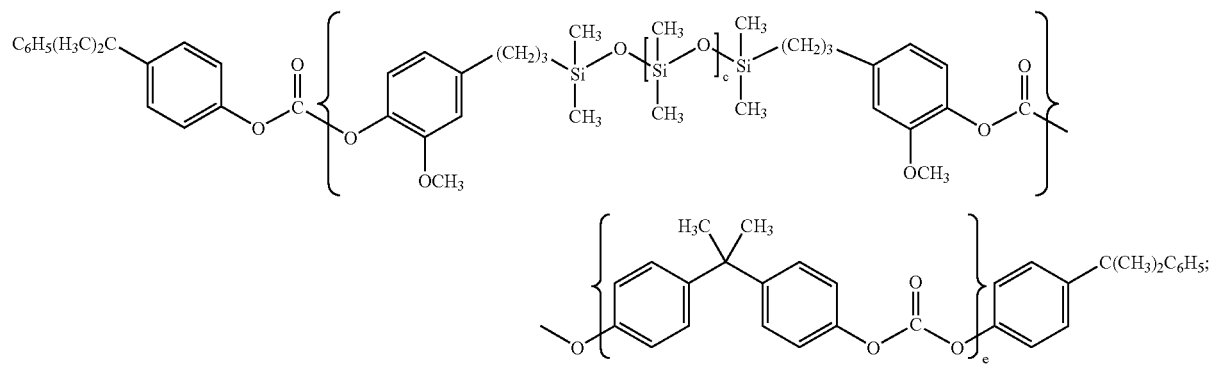

where "c" has a value of about 20 to about 60, "d" has a value from about 2 to about 3; "e" has a value from about 170 to about 180, and the siloxane blocks comprise from about 5 to about 10 percent by weight of the block copolymer.

The PPPBP/BPA PC copolymer refers to the polycarbonate copolymer prepared using a monomer mixture consisting of 75 mole percent of BPA and 25 mole percent of para, para-PPPBP, and has a glass transition temperature ($T_g$) of 189° C. The BHPM/BPA PC copolymer refers to a polycarbonate copolymer prepared using a monomer mixture consisting of 46 mole percent of 1-methyl-1,3-bis(4-hydroxyphenyl)-3-isopropylcyclohexane (abbreviated as "1,3-BHPM") and 54 mole percent of BPA, and has $T_g$ of 191° C.

All the ingredients in the formulation shown in Table 4 were weighed into a polyethylene bag using a digital weighing balance. All the ingredients were thoroughly mixed in the bag for 5 minutes. The mixed formulation was then melt mixed between 280-295 deg C. using an intermeshing, twin screw extruder (Coperion Model ZSK-25) equipped with a 25 millimeter diameter screw. The screw revolution was maintained at 500 RPM during the melt mixing. All the formulations were extruded into strands, which were subsequently cut into cylindrical shaped pellets using an in-line strand cutter.

The compounded pellets were dried at 80° C. for a minimum of 6 hours in a hot air circulated oven. Compounded pellets were then injection molded into standard test specimens using LT Demag 60 injection molding machine of L&T Make. The machine had a screw clamming capacity of 60 tons, a diameter of 25 mm and a shot capacity of 58 grams of polystyrene. Barrel zones were electrically heated and were maintained between 280-300° C. and the screw speed was 100 RPM. The mold was maintained at 70° C. using an oil heated mold temperature controller.

All the test specimens were conditioned at 23° C. and 50 percent relative humidity for a minimum of 48 hours before performing the testing. For impact testing, specimens were conditioned for a minimum of 24 hours after the notch cutting. Uni-axial tensile testing was done using an Instron Universal Testing Machine (Model No 5566, motor-driven test frame) in accordance with ISO 527 test method. Notched izod impact (NII) was determined in accordance with ISO 180A test protocol. The test was done using a CEAST Impact Tester using a 5.5 joule hammer. Values reported are in kilojoules per meter square. Heat distortion temperature (HDT) determination was carried out. HDT was measured in accordance with ISO 75 test method, by applying the load (1.8 MPa) edgewise on the sample after measuring the sample dimensions. A CEAST Heat Distortion Temperature Tester (Model No-6921) equipped with a circulating silicone oil as the heating medium was used to measure HDT. The values are reported in ° C. Char content analysis was done using a Thermo gravimetric Analyzer by heating the sample from room temperature to 800° C. at a rate of 20° C. per minute under nitrogen. The weight of the sample at 750° C. (that is, the temperature at which the plot of sample weight versus temperature levels off) was, taken as the final char content.

Melt volumetric flow rate (abbreviated as MVR) was measured in accordance with ISO 1133 test protocol using a CEAST Melt volumetric flow rate/melt flow rate testing machine. The processibility of a thermoplastic polymer composition can be expressed, for example, by its melt volume rate (hereinafter sometimes referred to as "MVR") value. In the present disclosure, MVR is defined as the volume of a sample that passes though an orifice with a piston when a sample of about 6-7 grams of the sample is placed under a constant load of 1.2 kilograms at about 300° C. and a dwell time of about 5 minutes. A higher value generally means the polymer composition is easier to process. MVR test samples were pre-dried for a minimum of 3 hours at 80° C. in a hot air circulated oven. MVR values are reported in cubic centimeters per 10 minutes.

Total flame out time (FOT) measurements were carried out on the molded specimens (1.6 millimeters thick, 13 millimeters wide, and 125 millimeters in length) in accordance with Underwriter Laboratories UL-94 Vertical Burn Test procedure dated, Jul. 29, 1997 as follows.

Molded specimens were clamped vertically with the help of a stand and on the rear side of which a mirror is placed to observe if the bars are burning at the backside so that the total flame out time is captured. A cotton layer was placed under the clamped bar as per the test protocol to check if any of the drips ignited the cotton layer. The test burner was applied to the bottom of the bar for 10 seconds. Then the flame was removed and burning time ($T_1$) (that is, the time required for the sample to self-extinguish) was recorded. As soon as the flame extinguished, the flame was re-applied immediately for another 10 seconds. Again the burning time (T2) was recorded. The FOT is then given by ($T_1+T_2$). The burning time after each flame application and ignition of the cotton layer was interpreted into a UL-94 flammability rating. A V-0 rating or an average FOT of less than 10 seconds indicates that the material has the best flame retardance. A V-1 rating is assigned for an average FOT value of between 10 to less than 30 seconds. When the specimen exhibits both dripping characteristics and ignition of the cotton, then the fire retardance is rated as V-2. Any specimen that could not be rated as per the above interpretation has been designated as "NR (not rated)".

Comparative Example 1

In this example, a prior art process was employed to isolate a para, para-PPPBP product.

The prior art process included refluxing a mixture of phenolphthalein (20 grams (g)), aniline hydrochloride (20 g), and 60 ml of aniline at a temperature from about 180° C. to about 185° C. for 5 hours under nitrogen. The dark solution was then stirred into a mixture of 100 grams of ice and 70 grams of concentrated HCl. The violet crystalline product was filtered off and washed with water. The crystals were then dissolved in ice-cold 10% sodium hydroxide solution. The solution was treated with 0.2 g active carbon, and then filtered. By drop-wise addition of concentrated HCl into the stirred batch, the color changed to a bright pink, then to a pure white, thick slurry with a pH of 3-4. The precipitated phenolphthalein anilide was then washed neutral with water and dried under vacuum at 70° C. The crude crystals gave a melting point of 288-291° C. with a yield of 79%. Double recrystallization from ethanol, followed by drying the crystals under vacuum at 150° C. gave the product. The results are shown in Table 1.

Comparative Example 2

The procedure described in Comparative Example 1 was repeated except that the water by-product was removed. The results are shown in Table 1.

Comparative Example 3

In this Example, phenolphthalein and aniline were reacted in the presence of hydrochloric acid. The reaction was carried out without removing the water by-product.

Phenolphthalein (38.1 grams), aniline (65 milliliters), and concentrated hydrochloric acid (20.5 milliliters) were charged into a reaction vessel and heated such that the temperature of the reaction mixture was 155° C.-165° C. The temperature of the reaction was adjusted to 155-165 C. After being heated for about 14-15 hours, the reaction mixture was poured into a mixture of hydrochloric acid and water. The solid product, which precipitated, was collected by filtration. Analysis of the solid product by HPLC indicated about 6 area percent of para,para-PPPBP and about 93 area percent of phenolphthalein, wherein ortho, para-PPPBP was not detected (less than 10 parts per million, the detection limit of the HPLC method). The results are shown in Table 1.

Comparative Examples 4 and 5

Polymerization runs were carried out using the procedure described in Example 2 below with the para,para-PPPBP prepared in accordance with Comparative Examples 1 and 2, respectively. The molecular weights of the polycarbonate prepared by this method and the YI of films prepared by solution casting of the polycarbonates are shown in Table 2.

Comparative Example 6

This Example describes the preparation of a polycarbonate copolymer using the same method as disclosed in Example 4 below, with a para, para-PPPBP monomer prepared in accordance with Comparative Example 2.

Comparative Examples 7-10

These examples illustrate the various polymer blend formulations that did not include the para,para-PPPBP/BPA polycarbonate. The formulations and results are shown in Table 4.

Example 1

This Example describes the preparation of para,para-PPPBP containing less than or equal to about 1,000 parts per million of ortho, para-PPPBP isomer impurity.

Phenolphthalein (318 grams), aniline (65 milliliters), and concentrated hydrochloric acid (20.5 milliliters) were taken in a reaction flask fitted with a Dean Stark condenser. The reaction mass was heated to an internal temperature of 155° C.-165° C. Water was collected during the course of the reaction. After being heated at this temperature for 14-15 hours, the reaction mixture was poured into a mixture of hydrochloric acid and water. The crude product, which precipitated, was collected by filtration and dissolved in an aqueous sodium hydroxide solution containing activated charcoal. After being stirred for about 30 minutes, the mixture was then filtered to remove the charcoal. The charcoal treatment step was repeated once more, and the resulting filtrate was treated with concentrated hydrochloric acid to precipitate para, para-PPPBP as a white solid, which was then filtered. The solid product was refluxed in methanol (approximately four volumes of methanol were taken relative to the volume of the solid product) for about an hour, cooled, and filtered to provide the final product which was found by HPLC analysis to have a para, para-PPPBP purity of 99.9 area percent. The yield of the isolated product was 80 to 82 percent of theory. The results are shown in Table 1, where "ND" indicates, "not detected".

Example 2

This Example describes the general melt transesterification method used for preparing polycarbonate copolymers using 47 weight percent of diphenyl carbonate and 53 weight percent of a monomer mixture consisting of 75 weight percent of BPA and 25 weight percent of the purified para,para-PPPBP prepared in accordance with Example 1.

A glass polymerization reactor was passivated by soaking the reactor in a bath containing 1 molar aqueous hydrochloric acid solution. After 24 hours, the reactor was thoroughly rinsed with demineralized water, and finally, with deionized water to ensure that all traces of acid and other contaminants were removed. The reactor was then thoroughly dried and charged with the appropriate amounts of the purified para, para-PPPBP monomer or a monomer mixture comprising the purified para,para-PPPBP and diphenyl carbonate monomers. The reactor was then mounted in a polymerization assembly and checked to ensure that no leaks were present. The catalyst solutions ($2.5 \times 10^4$ mol of aqueous tetramethylammonium hydroxide and $5 \times 10^{-6}$ mole of aqueous sodium hydroxide), as prepared above, were then introduced into the reactor using a syringe. The atmosphere inside the reactor was then evacuated using a vacuum source and purged with nitrogen. This cycle was repeated 3 times after which the contents of the reactor were heated to melt the monomer mixture. When the temperature of the mixture reached about 180° C. to about 190° C., the stirrer in the reactor was turned on and adjusted to about 40 to about 80 revolutions per minute (rpm) to ensure that the entire solid mass fully melted, a process that usually took about 15 to about 20 minutes. Next, the reaction mixture was heated to a temperature of about 230° C., while the pressure inside the reactor was adjusted to about 170 millibar using a vacuum source. This temperature-pressure-time regime was designated as P1. After stirring the reaction mass at this condition for about 1 hour, the reaction temperature was raised to about 270° C. while readjusting the pressure to around 20 millibar. After being maintained at this condition, designated as P2, for about 30 minutes, the temperature of the reaction mixture was raised to 300° C. while bringing the pressure down to less than or equal to about 1 millibar. After being maintained at this condition, designated as P3, for about 30 minutes, the temperature of the reaction mixture was raised to 300° C. while bringing the pressure down to less than or equal to about 1 millibar. After being maintained at this condition, designated as P4, for about 30 minutes, the temperature of the reaction mixture was raised to about 315° C. while bringing the pressure down to less than or equal to about 1 millibar. After allowing the reaction to proceed under these conditions, designated as P5, for about 10 minutes to about 20 minutes, the pressure inside the reactor was brought to atmospheric pressure and the reactor was vented to relieve any excess pressure. Product isolation was accomplished by breaking the glass nipple at the bottom of the reactor and collecting the material. In the cases where the product was of a very high molecular weight, the hot molten polymer was dropped down by pressurizing the reactor with nitrogen gas.

Example 3

This Example describes the melt transesterification method used for preparing polycarbonate copolymer using 55 weight percent of bismethylsalicyl carbonate and 45 weight percent of a monomer mixture comprising 75 weight percent of BPA and 25 weight percent of purified para,para-PPPBP (prepared as described in Example 1).

The same procedure as described above was used to charge the necessary reaction ingredients into the reactor. However, after the heating step to fully melt the monomer, the reaction mixture was heated to a temperature of about 210° C. at atmospheric pressure (about 910 millibar). After stirring the reaction mass at this condition for about 10 minutes, the pressure was reduced to about 100 millibars, and maintained at this condition for about 15 minutes. Next, the reaction mixture was heated to a temperature of about 310° C. while bring the pressure down to less than or equal to about 1 millibar. After being stirred under these conditions for about 15 minutes, the pressure inside the reactor was brought to atmospheric pressure and the reactor was vented to relieve any excess pressure. Product isolation was accomplished using the same procedure as described in Example 2.

The procedure described hereinabove was used to prepare polycarbonate copolymers having $M_w$ from about 45,000 to about 75,000.

Example 4

This Example describes the general procedure for the interfacial polymerization method using a monomer mixture comprising a 75:25 mole ratio of purified para,para-PPPBP (prepared in accordance with method described in Example 1) and BPA, respectively. The procedure used here is as described in U.S. Pat. No. 5,804,525, where the monomer mixture (as described above) and para-cumylphenol was reacted with phosgene in methylene chloride in the presence of tetrabutylammonium bromide. During addition of phosgene, the pH of the reaction mixture was maintained at about 10.5 by slow addition of aqueous sodium hydroxide. After phosgene addition, triethylamine was added to react out trace levels of chloroformate derivatives present in the reaction mixture. The polycarbonate thus prepared had the following physical properties: YI (yellowness index, ASTM D1925): 9; Notched izod at ambient temperature (ASTM D256): 4.9 foot-pound per inch; Glass transition temperature: 191° C.; Delta YI (ASTM D1925) of molded article after heat aging in air in an oven maintained at 155° C. -160° C. for 500 hours: less than 2; Delta YI (ASTM D1925) after heat aging in air in an oven maintained at 120° C. for 500 hours: less than 0.5.

TABLE 1

| | HPLC analysis (Area percent) | | |
|---|---|---|---|
| Example | para, para-PPPBP | Phenolphthalein | ortho, para-PPPBP |
| 1* | 97.5 | 0.5 | 2 |
| 2* | 98.5 | 0.11 | 1.35 |
| 3* | 6.2 | 93.1 | ND |
| 1 | 99.9 | 0.05 | ND |

*Indicates Comparative Example.

TABLE 2

| Polymerization Run Example Number | para, para-PPPBP Example Number | $M_w$ of polycarbonate (Daltons) | YI of polycarbonate (article) |
|---|---|---|---|
| 4* | 1* | 21,000 | 6.3 (film) |
| 5* | 2* | 19,000 | 4.3 (film) |
| 2 | 1 | 30,000 | 0.8 (film) |

TABLE 2-continued

| Polymerization Run Example Number | para, para-PPPBP Example Number | $M_w$ of polycarbonate (Daltons) | YI of polycarbonate (article) |
|---|---|---|---|
| 3 | 1 | 63,000 | 0.6 (film) |
| 4 | 1 | 62,000 | <1 (film); 9 (molded plaque) |
| 6* | 2* | 44,000 | 59 (molded plaque) |

*Indicates Comparative Example.

Table 1 shows the effect of the purity of the 2-hydrocarbyl-3,3-bis(4-hydroxyaryl)phthalimidines on the molecular weight and yellowness indices of films of the polymers derived using these phthalimidines as a comonomer with bisphenol A. Comparative Examples 1 and 2 indicate that a higher level of the 2-hydrocarbyl-3,3-{(4-hydroxyaryl)(2-hydroxyaryl)}phthalimidine impurity (or sometimes herein generally referred to as "ortho, para-PPPBP impurity") in the para,para-PPPBP comonomer results in a lower molecular weight and a relatively higher film yellowness index for the polymer. Without wishing to be bound by theory, it is believed that the ortho, paraPPPBP impurity, being relatively more sterically hindered than the corresponding para,para-phthalimidine isomer acts as a chain termination agent, thereby limiting polymer chain length and molecular weight. However, Example 1 shows that when para,para-PPPBP with no detectable (by HPLC) level of the ortho, para-impurity is copolymerized with BPA, the polymer weight average molecular weight is substantially higher (31,000). Furthermore, the polymer film has a relatively much lower yellowness index of 0.8. Comparative Example 3 shows that even if the reaction temperature is maintained at about 155° C. to 165° C., if water is not removed during the reaction to form para,para-PPPBP, the reaction gives a very poor yield (about 6 area percent) of para,para-PPPBP.

Moreover, when the compound (IV) was prepared in accordance with the procedure of Comparative Example 1, wherein phenolphthalein and excess aniline are heated under reflux in a nitrogen atmosphere for about 5 hours without removal of water, such that the reaction temperature is about 180° C. to about 185° C., the para, para-PPPBP that was isolated after the double crystallization from ethanol contained about 2.5 area percent of an undesired side-product that has been analytically determined to be isomeric ortho, para-PPPBP.

On the other hand, if the reaction is carried out in the same manner as described in Comparative Example 1, but the water by-product is distilled out over the same period of about 5 hours, HPLC analysis indicated that the isolated product contains about 98.5 area percent of para,para-PPPBP, about 0.11 area percent of phenolphthalein, and about 1.35 area percent of the impurity compound (IV). This indicates that water removal is necessary to lower the formation of compound (IV). However, when the reaction is conducted using a reaction temperature of about 160° C. to about 165° C., water removal takes about 14 hours, and the impurity (IV) was undetectable in the isolated para, para-PPPBP product relative to the measurement sensitivity of the HPLC method (detection limit of 10 parts per million for compound (IV)). Furthermore, the product only contains about 0.05 area percent of phenolphthalein. In contrast, when the reaction was conducted at a reaction temperature of about 160° C. to about 165° C., but the water was not removed, HPLC analysis of the reaction mixture after 14 hours of heating indicated formation of only about 6.2 area percent of para, para-PPPBP with the majority (about 92 area percent) of phenolphthalein starting material remaining unreacted. These results clearly indicate that the preferred method for forming para, para-PPPBP in high isolated yield and high isomeric purity is to maintain the reaction temperature at about 160° C. to about 165° C. with water removal over a period of about 14 hours. Under such conditions, utilization of phenolphthalein for selectively forming para, para-PPPBP is enhanced, and formation of the ortho, para-PPPBP is minimized. These techniques can be suitably adapted to prepare the other 2-hydrocarbyl-3,3-bis (4-hydroxyaryl)phthalimidines described previously.

The results shown in Table 1 (Example 1), and Table 2, (Examples 2 and 4) clearly indicate that purified para,para-PPPBP is useful for preparing polycarbonates of high molecular weight (e.g., $M_w$ of 62,000), which are valuable for producing films and molded articles having a yellowness index of less than 10. Moreover, the molded articles show excellent resistance to heat aging, as shown in Example 4, thus making such polycarbonates valuable for high heat applications.

Examples 5-7

These examples illustrate the various polymer blend formulations that included varying amounts of the para,para-PPPBP/BPA polycarbonate. The formulations and results are shown in Table 4.

polycarbonate copolymer also gives V-0 fire retardance (see Example 7), however, use of 7 weight percent of the para,para-PPPBP/BPA polycarbonate copolymer to the polycarbonate-ABS resin blend leads to a V-1 fire retardant composition (See Example 6). Therefore, it appears that for polycarbonate-ABS resin blends, the transition from V-0 to V-1 fire retardance occurs when the amount of the para, para-PPPBP/BPA polycarbonate copolymer is varied from 7-10 weight percent. Further, comparison of Example 5 and Comparative Example 6 shows that use of the para,para-PPPBP/BPA polycarbonate as a fire retardant additive gives an increase in the HDT of about 15° C., thereby clearly showing the plasticizing effect of the BPADP type fire retardant additive. Additionally, the composition of Example 5 shows a significantly improved NII (at ambient temperature) value of 25.6 kilojoules per meter square, as compared to the value of 16.8 kilojoules per meter square for the composition of Comparative Example 7.

Comparative Example 10 indicates that if the 1,3-BHPM/BPA polycarbonate copolymer with a $T_g$ of about 191° C., which is comparable to the $T_g$ (189° C.) of the para,para-PPPBP/BPA polycarbonate copolymer is used, poor fire-retardance was observed, and therefore the result could not be classified under the UL94 rating system. Hence, the fire retardant activity cannot be generalized to any polycarbonate polymer having a relatively high $T_g$, such as those polymers having a $T_g$ of around 190° C. Comparing the data obtained from Comparative Example 9 and Example 5, it can be seen that the use of para,para-PPPBP/BPA polycar-

TABLE 4

| | Compositions and Examples | | | | | | | |
|---|---|---|---|---|---|---|---|---|
| | A | B | C | D | E | F | G | H |
| | 5 | 6* | 7* | 8* | 9* | 10* | 6 | 7 |
| Raw materials | | | | | | | | |
| PC-105 | 80.4 | 90.4 | 94.4 | 92.4 | 80.4 | 80.4 | 87.4 | 84.4 |
| Liquid BPADP | 0 | 4 | 0 | 2 | 0 | 0 | 0 | 0 |
| Bulk ABS | 4 | 4 | 4 | 4 | 4 | 4 | 4 | 4 |
| Anti-drip additive | 1 | 1 | 1 | 1 | 1 | 1 | 1 | 1 |
| Anti-oxidant | 0.2 | 0.2 | 0.2 | 0.2 | 0.2 | 0.2 | 0.2 | 0.2 |
| Pentaerythritol tetrastearate | 0.4 | 0.4 | 0.4 | 0.4 | 0.4 | 0.4 | 0.4 | 0.4 |
| PC-ST | 0 | 0 | 0 | 0 | 14 | 0 | 0 | 0 |
| PPPBP/BPA PC copolymer | 14 | 0 | 0 | 0 | 0 | 0 | 7 | 10 |
| BHPM/BPA PC copolymer | 0 | 0 | 0 | 0 | 0 | 14 | 0 | 0 |
| Property Measured | | | | | | | | |
| Average FOT | 2.6 | 2.68 | 14.24 | 9.4 | 16.1 | 32.2 | 10.6 | 4.9 |
| UL94 rating | V0 | V0 | V1 | V1 | V1 | NR | V1 | V0 |
| NII (kJ/m$^2$) | 25.6 | 16.8 | 71.5 | 25.5 | 79.5 | 65.3 | 31.3 | 28.9 |
| Tensile Modulus (MPa) | 2338 | 2573 | 2417 | 2373 | 2279 | 2495 | 2314 | 2330 |
| Tensile Strength (MPa) | 62.1 | 63.83 | 58.3 | 60.3 | 57.5 | 63.9 | 60.5 | 60.7 |
| Yield Strain % | 6.1 | 5.8 | 5.9 | 5.6 | 6.0 | 7.1 | 6.0 | 5.9 |
| Break Stress (MPa) | 49 | 65.3 | 59.3 | 61.7 | 62.2 | 64.5 | 53.3 | 57.4 |
| Break Strain (percent) | 41 | 101.7 | 95 | 94.6 | 103.9 | 90.1 | 72.4 | 85.3 |
| MVR | 6.3 | 5.9 | 6.1 | 5.5 | 6.3 | 5 | 11.2 | 10.3 |
| Char Yield (weight percent) | 25.7 | 20.1 | 19.9 | 19.7 | 21.3 | 19.6 | 22.1 | 20.9 |
| HDT (° C.) | 124 | 109.1 | 121.8 | 114.4 | 117.2 | 124.7 | 121 | 121.6 |

*denotes comparative example

The data as presented in Table 4 shows that addition of 10 to 14 weight percent of the para, para-PPPBP/BPA polycarbonate copolymer to a BPA polycarbonate-ABS resin blend advantageously and unexpectedly leads to a V-0 fire-retardant composition, most notably achieved without the use of any phosphorus-containing compound (such as BPADP) as a fire retardant additive. Use of 10 weight percent of the bonate copolymer as a polymeric fire retardant additive gives superior fire retardance, as compared with using the PC-ST copolymer, but without an added organic phosphorus compound. Organosiloxane-polycarbonate block copolymer, such as PC-ST have previously been used as a synergist in conjunction with an organic phosphorus compound for preparing fire-retardant polymer compositions.

It also appears that when polycarbonates comprising structural units derived from para,para-PPPBP are incorporated in the BPA polycarbonate-ABS resin blend, the resulting compositions show a surprisingly higher MVR (6.3 in Example 5), as compared to compositions which do not contain the para,para-PPPBP/BPA polycarbonate (5.1 in Comparative Example 6). Therefore, the present disclosure enables one to produce V-0 fire-retardant polymer blends that not only have higher HDT values, but also are relatively easier to process.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

The invention claimed is:

1. A polymer blend consisting essentially of at least one thermoplastic polymer and a polymer comprising structural units derived from a 2-aryl-3,3-bis(4-hydroxyaryl)phthalimidine, wherein the at least one thermoplastic polymer and the polymer comprising the structural units are different and wherein the polymer comprising structural units derived from a 2-aryl-3,3-bis(4-hydroxyaryl)phthalimidine has a yellowness index of less than 10 as measured on a 3 millimeter thick plaque in accordance with ASTM D1925.

2. The polymer blend of claim 1, wherein the at least one thermoplastic polymer comprises a vinyl polymer, a rubber-modified graft copolymer, an acrylic polymer, polyacrylonitrile, a polystyrene, a polyolefin, a polyester, a polyurethane, a polyamide, a polysulfone, a polyimide, a polyetherimide, a polyphenylene ether, a polyphenylene sulfide, a polyether ketone, a polyether ether ketone, an ABS resin, an ASA resin, a polyethersulfone, a poly(alkenylaromatic) polymer, a polybutadiene, polyacetal, a polycarbonate, a polyphenylene ether, an ethylene-vinyl acetate copolymer, a polyvinyl acetate, a liquid crystal polymer, an ethylene-tetrafluoroethylene copolymer, an aromatic polyester, a polyvinyl fluoride, a polyvinylidene fluoride, a polyvinylidene chloride, a polycarbonate-polyorganosiloxane block copolymer, a copolymer comprising an aromatic ester, an estercarbonate, and a carbonate repeat unit, and mixtures thereof.

3. The polymer blend of claim 2, wherein said polycarbonate comprises structural units derived from at least one aromatic dihydroxy compound of the formula:

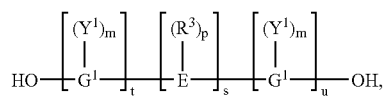

wherein each $G^1$ is an independently aromatic group; E is selected from the group consisting of an alkylene group, an alkylidene group, a cycloaliphatic group, a sulfur-containing linkage group, a phosphorus-containing linkage group, an ether linkage group, a carbonyl group, a tertiary nitrogen group, and a silicon-containing linkage group; $R^3$ is a hydrogen or a monovalent hydrocarbyl group each; $Y^1$ is independently selected from the groups consisting of a monovalent hydrocarbon group, an alkenyl group, an allyl group, a halogen, an oxy group and a nitro group; each m is independently a whole number from zero through the number of positions on each respective $G^1$ available for substitution; p is a whole number from zero through the number of positions on E available for substitution; t is a natural number greater than or equal to one; s is either zero or one; and u is a whole number.

4. The polymer blend of claim 3, wherein the at least one aromatic dihydroxy compound is selected from the group consisting of 4,4'-(3,3,5-trimethylcyclohexylidene)diphenol, 4,4'-bis(3,5-dimethyl)diphenol, 1,1-bis(4-hydroxy-3-methylphenyl)cyclohexane, 1,1-bis(4'-hydroxy-3'methylphenyl)cyclohexane, 4,4'-[1-methyl-4-(1-methylethyl)-1,3-cyclohexandiyl]bisphenol, 4-[1-[3-(4-hydroxyphenyl)-4-methylcyclohexyl]-1-methyl-ethyl]-phenol, 3,8-dihydroxy-5a,10b-diphenylcoumarano-2',3',2,3-coumarane, 2-phenyl-3,3-bis(4-hydroxyphenyl)phthalimidine, 4,4-bis(4-hydroxyphenyl)heptane, 2,4'-dihydroxydiphenylmethane, bis(2-hydroxyphenyl)methane, bis(4-hydroxyphenyl)methane, bis(4-hydroxy-5-nitrophenyl)methane, bis(4-hydroxy-2,6-dimethyl-3-methoxyphenyl)methane, 1,1-bis(4-hydroxyphenyl)ethane, 1,1-bis(4-hydroxy-2-chlorophenyl)ethane, 2,2-bis(4-hydroxyphenyl)propane, 2,2-bis(3-phenyl-4-hydroxyphenyl)propane, 2,2-bis(4-hydroxy-3-methylphenyl)propane, 2,2-bis(4-hydroxy-3-ethylphenyl)propane, 2,2-bis(4-hydroxy-3-isopropylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl)cyclohexylmethane, 2,2-bis(4-hydroxyphenyl)-1-phenylpropane, 2,4'-dihydroxyphenyl sulfone, 4,4'-dihydroxydiphenylsulfone, 9,9-bis(4-hydroxyphenyl)fluorene, 4,4'dihydroxy-1,1-biphenyl, 2,6-dihydroxy naphthalene; hydroquinone; resorcinol, $C_{1-3}$ alkyl-substituted resorcinols, 3-(4-hydroxyphenyl)-1,1,3-trimethylindan-5-ol, 1-(4-hydroxyphenyl)-1,3,3-trimethylindan-5-ol, and 2,2,2',2'-tetrahydro-3,3,3',3'-tetramethyl-1,1'-spirobi[1H-indene]-6,6'-diol.

5. The polymer blend of claim 2, wherein the rubber modified graft copolymer comprises a discontinuous rubber phase dispersed in a continuous rigid thermoplastic phase, wherein at least a portion of the rigid thermoplastic phase is chemically grafted to the rubber phase.

6. The polymer blend of claim 5, wherein the rigid thermoplastic phase has a glass transition temperature of greater than about 25° C., and from about 10 to about 90 weight percent of the rigid thermoplastic phase is chemically grafted to the rubber phase.

7. The polymer blend of claim 5, wherein the rubber phase comprises a polybutadiene rubber, poly(styrene-butadiene) rubber, poly(butyl acrylate) rubber, or ethylene-propylene-diene modified rubber; and the rigid thermoplastic phase comprises a styrene-acrylonitrile copolymer.

8. The polymer blend of claim 2, wherein the rubber modified graft copolymer comprises structural units derived from at least one of 1,3-butadiene, isoprene, or butyl acrylate.

9. The polymer blend of claim 1, wherein said thermoplastic polymer comprises homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, estercarbonate, and carbonate repeat units; and a polyetherketone.

10. The polymer blend of claim 1, wherein the at least one thermoplastic polymer comprises structural units derived from one or more vinyl aromatic monomers, or one or more monoethylenically unsaturated nitrile monomers.

11. The polymer blend of claim 1, wherein the at least one thermoplastic polymer comprises structural units derived from styrene and acrylonitrile.

12. The polymer blend of claim 1, wherein said 2-aryl-3,3-bis(4-hydroxyaryl)phthalimidine further comprises less than or equal to 1,000 parts per million of a substituted or an unsubstituted phenolphthalein relative to an overall weight of said 2-hydrocarbyl-3,3-bis(4-hydroxyaryl)phthalimidine.

13. The polymer blend of claim 1, wherein said 2-aryl-3,3-bis(4-hydroxyaryl)phthalimidine is a 2-phenyl-3,3-bis(4-hydroxyphenyl)phthalimidine.

14. The polymer blend of claim 13, wherein said 2-phenyl-3,3-bis(4-hydroxyphenyl)phthalimidine further comprises less than or equal to 1,000 parts per million of phenolphthalein relative to an overall weight of said 2-phenyl-3,3-bis(4-hydroxyphenyl)phthalimidine.

15. The polymer blend of claim 1, further comprising at least one impact modifier.

16. A molded article comprising the polymer blend of claim 1.

17. A molded article comprising a polymer blend, said polymer blend consisting essentially of:
   at least one thermoplastic polymer in an amount of 5 to 98 weight percent based on a total weight of the polymer blend, wherein the at least one thermoplastic polymer comprises vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, aromatic polyesters, polyestercarbonate, copolymers comprising aromatic ester, estercarbonate, and carbonate repeat units, mixtures; and blends comprising at least one of the foregoing polymers;
   at least one rubber-modified graft copolymer in an amount of 75 to 1 weight percent based on a total weight of the polymer blend; and
   a polycarbonate in an amount of 20 to 1 weight percent based on a total weight of the polymer blend, wherein the polycarbonate comprises structural units derived from a 2-aryl-3,3-bis(4-hydroxylaryl)phthalimidine.

18. The molded article of claim 17, wherein said 2-aryl-3,3-bis(4-hydroxylaryl)phthalimidine is 2-phenyl-3,3-bis(4-hydroxyphenyl)phthalimidine.

19. The molded article of claim 17, wherein said at least one thermoplastic polymer is bisphenol A homopolycarbonate.

20. A molded article comprising a polymer blend, said polymer blend consisting essentially of:
   a bisphenol A polycarbonate in an amount of 5 to 98 weight percent based on a total weight of the polymer blend;
   an acrylonitrile-butadiene-styrene resin in an amount of 75 to 1 weight percent based on a total weight of the polymer blend; and
   polycarbonate in an amount of 20 to 1 weight percent based on a total weight of the polymer blend, wherein the polycarbonate comprises structural units derived from a 2-phenyl-3-{(4-hydroxyphenyl)(2-hydroxyphenyl)}phthalimidine.

21. The molded article of claim 20, wherein said 2-phenyl-3,3-bis(4-hydroxyphenyl)phthalimidine further comprises less than or equal to 1,000 parts per million of 2-phenyl-3-{(4-hydroxyphenyl)(2-hydroxyphenyl)}phthalimidine relative to an overall weight of said 2-phenyl-3,3-bis(4-hydroxyphenyl)phthalimidine.

22. The molded article of claim 20, wherein said 2-phenyl-3,3-bis(4-hydroxyphenyl)phthalimidine further comprises less than or equal to 1,000 parts per million of phenolphthalein relative to an overall weight of said 2-phenyl-3,3-bis(4-hydroxyphenyl)phthalimidine.

23. A polymer blend comprising:
   at least one thermoplastic polymer, and
   a 2-phenyl-3,3-bis(4-hydroxyphenyl)phthalimidine/BPA polycarbonate copolymer in an amount greater than 7 weight percent of the total weight of the blend, wherein the polymer blend is free of a fire retardant phosphorous containing compound, and has at least a V-1 fire rating as measured in accordance with Underwriter Laboratories UL-94 Vertical Burn Test procedure dated Jul. 29, 1997, wherein the at least one thermoplastic polymer and the 2-phenyl-3,3-bis(4-hydroxyphenyl)phthalimidine/BPA polycarbonate copolymer are different, and wherein the 2-phenyl-3,3-bis(4-hydroxyphenyl)phthalimidine/BPA polycarbonate copolymer has a yellowness index of less than 10 as measured on a 3 millimeter thick plaque in accordance with ASTM D1925.

24. The polymer blend of claim 23, wherein said polymer blend has at least a V-0 fire rating as measured in accordance with Underwriter Laboratories UL-94 Vertical Burn Test procedure dated Jul. 29, 1997.

25. The polymer blend of claim 23, wherein said fire retardant phosphorus containing compound is selected from the group consisting of triphenylphosphate, tricresylphosphate, resorcinol bis(diphenylphosphate), tris(nonyl)phenylphosphate and bisphenol A diphosphate, and mixtures of the foregoing phosphorus containing compounds.

26. A polycarbonate-acrylonitrile-butadiene-styrene polymer blend comprising:
   a bisphenol A polycarbonate;
   an acrylonitrile-butadiene-styrene; and
   a 2-phenyl-3,3-bis(4-hydroxyphenyl)phthalimidine/BPA polycarbonate copolymer in an amount greater than 7 weight percent of the total weight of the blend, wherein the polycarbonate-acrylonitrile-butadiene-styrene polymer blend is free of a fire retardant phosphorous containing compound and has a V-0 fire rating as measured in accordance with Underwriter Laboratories UL-94 Vertical Burn Test procedure dated Jul. 29, 1997.

27. The polymer blend of claim 26, wherein said fire retardant phosphorus containing compound is selected from the group consisting of triphenylphosphate, tricresylphosphate, resorcinol bis(diphenylphosphate), tris(nonyl)phenylphosphate and bisphenol A diphosphate, and mixtures of the foregoing phosphorus containing compounds.

28. A polymer blend comprising at least one thermoplastic polymer and a polymer comprising structural units derived from a 2-aryl-3,3-bis(4-hydroxyaryl)phthalimidine, wherein the blend does not comprise a flame retardant, wherein the at least one polymer and the polymer comprising the structural units are different, and wherein the polymer comprising structural units derived from a 2-aryl-3,3-bis(4-hydroxyaryl)phthalimidine has a yellowness index of less than 10 as measured on a 3 millimeter thick plaque in accordance with ASTM D1925.

29. The polymer blend of claim 28, wherein said at least one thermoplastic polymer comprises a vinyl polymer, a rubber-modified graft copolymer, an acrylic polymer, polyacrylonitrile, a polystyrene, a polyolefin, a polyester, a polyurethane, a polyamide, a polysulfone, a polyimide, a polyetherimide, a polyphenylene ether, a polyphenylene sulfide, a polyether ketone, a polyether ether ketone, an ABS resin, an ASA resin, a polyethersulfone, a poly(alkenylaromatic) polymer, a polybutadiene, polyacetal, a polycarbonate, a polyphenylene ether, an ethylene-vinyl acetate copolymer, a polyvinyl acetate, a liquid crystal polymer, an ethylene-tetrafluoroethylene copolymer, an aromatic polyester, a polyvinyl fluoride, a polyvinylidene fluoride, a polyvinylidene chloride, a polycarbonate-polyorganosiloxane block copolymer, a copolymer comprising an aromatic ester, an estercarbonate, and a carbonate repeat unit, and mixtures thereof.

30. The polymer blend of claim 28, wherein said 2-aryl-3,3-bis(4-hydroxyaryl)phthalimidine is a 2-phenyl-3,3-bis(4-hydroxyphenyl)phthalimidine.

31. The polymer blend of claim 30, wherein said 2-phenyl-3,3-bis(4-hydroxyphenyl)phthalimidine further comprises less than or equal to 1,000 parts per million of phenolphthalein relative to an overall weight of said 2-phenyl-3,3-bis(4-hydroxyphenyl)phthalimidine.

* * * * *